United States Patent
Miller et al.

(10) Patent No.: US 12,337,132 B2
(45) Date of Patent: Jun. 24, 2025

(54) APPARATUS AND METHODS TO COMMUNICATE FLUIDS AND/OR SUPPORT INTRAOSSEOUS DEVICES

(71) Applicant: Teleflex Life Sciences II LLC, Wilmington, DE (US)

(72) Inventors: Larry J. Miller, Spring Branch, TX (US); David S. Bolleter, San Antonio, TX (US); Robert W. Titkemeyer, San Antonio, TX (US); Joseph J. Manno, La Jolla, CA (US); Matthew T. Harmon, Santa Cruz, CA (US); Bruce J. Richardson, Santa Cruz, CA (US); Gary Emerson Hart, Santa Cruz, CA (US)

(73) Assignee: TELEFLEX LIFE SCIENCES II LLC, Wilmington, DE (US)

( * ) Notice: Subject to any disclaimer, the term of this patent is extended or adjusted under 35 U.S.C. 154(b) by 0 days.

(21) Appl. No.: 18/111,824

(22) Filed: Feb. 20, 2023

(65) Prior Publication Data
US 2023/0191100 A1 Jun. 22, 2023

Related U.S. Application Data

(60) Division of application No. 16/372,056, filed on Apr. 1, 2019, now Pat. No. 11,583,668, which is a division
(Continued)

(51) Int. Cl.
*A61M 39/02* (2006.01)
*A61B 17/34* (2006.01)
(Continued)

(52) U.S. Cl.
CPC ......... *A61M 39/02* (2013.01); *A61B 17/3472* (2013.01); *A61B 17/3498* (2013.01);
(Continued)

(58) Field of Classification Search
CPC .. A61M 39/02; A61M 5/158; A61M 39/0247; A61M 39/26; A61M 39/10;
(Continued)

(56) References Cited

U.S. PATENT DOCUMENTS

| 2,223,219 A | 11/1940 | Mayerovitz |
| 2,317,648 A | 4/1943 | Siqveland |

(Continued)

FOREIGN PATENT DOCUMENTS

| CA | 2138842 A1 | 6/1996 |
| CA | 2454600 A1 | 2/2003 |

(Continued)

OTHER PUBLICATIONS

"Proven reliability for quality bone marrow samples", Special Procedures, Cardinal Health, 6 pages, 2003.
(Continued)

*Primary Examiner* — Theodore J Stigell
(74) *Attorney, Agent, or Firm* — BakerHostetler

(57) ABSTRACT

Fluid communication devices and supporting structures may be provided for use with intraosseous devices. Apparatus and methods may also be provided to communicate fluids with an intraosseous device.

15 Claims, 14 Drawing Sheets

Related U.S. Application Data of application No. 14/643,839, filed on Mar. 10, 2015, now Pat. No. 10,258,783, which is a continuation of application No. 11/619,390, filed on Jan. 3, 2007, now Pat. No. 8,974,410.

(60) Provisional application No. 60/863,521, filed on Oct. 30, 2006.

(51) Int. Cl.
- *A61M 5/158* (2006.01)
- *A61M 39/10* (2006.01)
- *A61M 39/26* (2006.01)

(52) U.S. Cl.
CPC ........ *A61M 5/158* (2013.01); *A61M 39/0247* (2013.01); *A61M 39/26* (2013.01); *A61B 2017/3492* (2013.01); *A61M 2005/1581* (2013.01); *A61M 2005/1585* (2013.01); *A61M 2039/025* (2013.01); *A61M 2039/0273* (2013.01); *A61M 2039/0276* (2013.01); *A61M 39/10* (2013.01); *A61M 2210/02* (2013.01)

(58) Field of Classification Search
CPC .. A61M 2005/1581; A61M 2005/1585; A61M 2039/025; A61M 2039/0273; A61M 2039/0276; A61M 2210/02; A61M 2025/024; A61B 17/3472; A61B 17/3498; A61B 2017/3492

See application file for complete search history.

(56) References Cited

U.S. PATENT DOCUMENTS

| | | |
|---|---|---|
| 2,419,045 A | 4/1947 | Whittaker |
| 2,773,501 A | 12/1956 | Young |
| 3,104,448 A | 9/1963 | Morrow et al. |
| 3,120,845 A | 2/1964 | Horner |
| 3,173,417 A | 3/1965 | Horner |
| 3,175,554 A | 3/1965 | Stewart |
| 3,507,276 A | 4/1970 | Burgess et al. |
| 3,543,966 A | 12/1970 | Ryan et al. |
| 3,815,605 A | 6/1974 | Schmidt et al. |
| 3,835,860 A | 9/1974 | Garretson |
| 3,893,445 A | 7/1975 | Hofsess |
| 3,991,765 A | 11/1976 | Cohen |
| 4,021,920 A | 5/1977 | Kirschner et al. |
| 4,099,518 A | 7/1978 | Baylis et al. |
| 4,124,026 A | 11/1978 | Berner et al. |
| 4,142,517 A | 3/1979 | Contreras et al. |
| 4,170,993 A | 10/1979 | Alvarez |
| 4,185,619 A | 1/1980 | Reiss |
| 4,194,505 A | 3/1980 | Schmitz |
| 4,258,722 A | 3/1981 | Sessions et al. |
| 4,262,676 A | 4/1981 | Jamshidi |
| 4,306,570 A | 12/1981 | Matthews |
| 4,333,459 A | 6/1982 | Becker |
| 4,381,777 A | 5/1983 | Garnier |
| 4,441,563 A | 4/1984 | Walton, II |
| 4,469,109 A | 9/1984 | Mehl |
| 4,484,577 A | 11/1984 | Sackner et al. |
| 4,543,966 A | 10/1985 | Islam et al. |
| 4,553,539 A | 11/1985 | Morris |
| 4,605,011 A | 8/1986 | Naslund |
| 4,620,539 A | 11/1986 | Andrews et al. |
| 4,646,731 A | 3/1987 | Brower |
| 4,654,492 A | 3/1987 | Koerner et al. |
| 4,655,226 A | 4/1987 | Lee |
| 4,659,329 A | 4/1987 | Annis |
| 4,692,073 A | 9/1987 | Martindell |
| 4,713,061 A | 12/1987 | Tarello et al. |
| 4,716,901 A | 1/1988 | Jackson et al. |
| 4,723,945 A | 2/1988 | Theiling |
| 4,758,225 A | 7/1988 | Cox et al. |
| 4,772,261 A | 9/1988 | Von et al. |
| 4,787,893 A | 11/1988 | Villette |
| 4,793,363 A | 12/1988 | Ausherman et al. |
| 4,838,282 A | 6/1989 | Strasser et al. |
| 4,867,158 A | 9/1989 | Sugg |
| 4,919,146 A | 4/1990 | Rhinehart et al. |
| 4,921,013 A | 5/1990 | Spalink et al. |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,986,279 A | 1/1991 | O'Neill |
| 5,002,546 A | 3/1991 | Romano |
| 5,025,797 A | 6/1991 | Baran |
| 5,036,860 A | 8/1991 | Leigh et al. |
| 5,057,085 A | 10/1991 | Kopans |
| 5,074,311 A | 12/1991 | Hasson |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,518 A | 8/1992 | Mersch |
| 5,139,500 A | 8/1992 | Schwartz |
| RE34,056 E | 9/1992 | Lindgren et al. |
| 5,172,701 A | 12/1992 | Leigh |
| 5,172,702 A | 12/1992 | Leigh et al. |
| 5,176,643 A | 1/1993 | Kramer et al. |
| 5,195,985 A | 3/1993 | Hall |
| 5,203,056 A | 4/1993 | Funk et al. |
| 5,207,697 A | 5/1993 | Carusillo et al. |
| 5,249,583 A | 10/1993 | Mallaby |
| 5,257,632 A | 11/1993 | Turkel et al. |
| 5,263,939 A * | 11/1993 | Wortrich ................ A61B 17/34 604/174 |
| 5,269,785 A | 12/1993 | Bonutti |
| 5,279,306 A | 1/1994 | Mehl |
| 5,312,364 A | 5/1994 | Jacobs |
| 5,312,408 A | 5/1994 | Brown |
| 5,324,300 A | 6/1994 | Elias et al. |
| 5,332,398 A | 7/1994 | Miller et al. |
| 5,333,790 A | 8/1994 | Christopher |
| 5,341,823 A | 8/1994 | Manosalva et al. |
| 5,348,022 A | 9/1994 | Leigh et al. |
| 5,357,974 A | 10/1994 | Baldridge |
| 5,368,046 A | 11/1994 | Scarfone et al. |
| 5,372,583 A | 12/1994 | Roberts et al. |
| 5,383,859 A | 1/1995 | Sewell, Jr. |
| 5,385,553 A | 1/1995 | Hart et al. |
| 5,400,798 A | 3/1995 | Baran |
| 5,405,362 A | 4/1995 | Kramer et al. |
| 5,423,824 A | 6/1995 | Akerfeldt et al. |
| 5,431,655 A | 7/1995 | Melker et al. |
| 5,451,210 A | 9/1995 | Kramer et al. |
| 5,484,442 A | 1/1996 | Melker et al. |
| D369,858 S | 5/1996 | Baker et al. |
| 5,526,821 A | 6/1996 | Jamshidi |
| 5,529,580 A | 6/1996 | Kusunoki et al. |
| 5,554,154 A | 9/1996 | Rosenberg |
| 5,556,399 A | 9/1996 | Huebner |
| 5,558,737 A | 9/1996 | Brown et al. |
| 5,586,847 A | 12/1996 | Mattern et al. |
| 5,591,188 A | 1/1997 | Waisman |
| 5,595,186 A | 1/1997 | Rubinstein et al. |
| 5,601,559 A | 2/1997 | Melker et al. |
| 5,632,747 A | 5/1997 | Scarborough et al. |
| 5,713,368 A | 2/1998 | Leigh |
| 5,724,873 A | 3/1998 | Hillinger |
| 5,733,262 A | 3/1998 | Paul |
| 5,752,923 A | 5/1998 | Terwilliger |
| 5,762,639 A | 6/1998 | Gibbs |
| 5,769,086 A | 6/1998 | Ritchart et al. |
| 5,779,708 A | 7/1998 | Wu |
| 5,800,389 A | 9/1998 | Burney et al. |
| 5,807,277 A | 9/1998 | Swaim |
| 5,810,826 A | 9/1998 | Angstrom et al. |
| 5,817,052 A | 10/1998 | Johnson et al. |
| 5,823,970 A | 10/1998 | Terwilliger |
| D403,405 S | 12/1998 | Terwilliger |
| 5,858,005 A | 1/1999 | Kriesel |

(56) References Cited

U.S. PATENT DOCUMENTS

| | | |
|---|---|---|
| 5,868,711 A | 2/1999 | Kramer et al. |
| 5,873,510 A | 2/1999 | Hirai et al. |
| 5,885,226 A | 3/1999 | Rubinstein et al. |
| 5,891,085 A | 4/1999 | Lilley et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,924,864 A | 7/1999 | Loge et al. |
| 5,927,976 A | 7/1999 | Wu |
| 5,928,238 A | 7/1999 | Scarborough et al. |
| 5,941,706 A | 8/1999 | Ura |
| 5,941,851 A | 8/1999 | Coffey et al. |
| 5,960,797 A | 10/1999 | Kramer et al. |
| 5,980,545 A | 11/1999 | Pacala et al. |
| 5,993,417 A | 11/1999 | Yerfino et al. |
| 5,993,454 A | 11/1999 | Longo |
| 6,007,496 A | 12/1999 | Brannon |
| 6,017,348 A | 1/2000 | Hart et al. |
| 6,018,094 A | 1/2000 | Fox |
| 6,022,324 A | 2/2000 | Skinner |
| 6,027,458 A | 2/2000 | Janssens |
| 6,033,369 A | 3/2000 | Goldenberg |
| 6,033,411 A | 3/2000 | Preissman |
| 6,063,037 A | 5/2000 | Mittermeier et al. |
| 6,080,115 A | 6/2000 | Rubinstein |
| 6,083,176 A | 7/2000 | Terwilliger |
| 6,086,544 A | 7/2000 | Hibner et al. |
| 6,096,042 A | 8/2000 | Herbert |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,134,477 A * | 10/2000 | Knuteson ............ A61N 1/0539 607/115 |
| 6,135,769 A | 10/2000 | Kwan |
| 6,159,163 A | 12/2000 | Strauss et al. |
| 6,162,203 A | 12/2000 | Haaga |
| 6,183,442 B1 | 2/2001 | Athanasiou et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming et al. |
| 6,309,358 B1 | 10/2001 | Okubo |
| 6,312,394 B1 | 11/2001 | Fleming, III |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,402,701 B1 | 6/2002 | Kaplan et al. |
| 6,419,490 B1 | 7/2002 | Kitchings Weathers, Jr. |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,468,248 B2 | 10/2002 | Gibbs |
| 6,478,751 B1 | 11/2002 | Krueger et al. |
| 6,488,636 B2 | 12/2002 | Bryan et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,540,694 B1 | 4/2003 | Van et al. |
| 6,547,511 B1 | 4/2003 | Adams |
| 6,547,561 B2 | 4/2003 | Meller et al. |
| 6,554,779 B2 | 4/2003 | Viola et al. |
| 6,555,212 B2 | 4/2003 | Boiocchi et al. |
| 6,582,399 B1 | 6/2003 | Smith et al. |
| 6,585,622 B1 | 7/2003 | Shum et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,626,848 B2 | 9/2003 | Neuenfeldt |
| 6,626,887 B1 | 9/2003 | Wu |
| 6,638,235 B2 | 10/2003 | Miller et al. |
| 6,656,133 B2 | 12/2003 | Voegele et al. |
| 6,689,072 B2 | 2/2004 | Kaplan et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,796,957 B2 | 9/2004 | Carpenter et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,905,486 B2 | 6/2005 | Gibbs |
| 6,930,461 B2 | 8/2005 | Rutkowski |
| 6,942,669 B2 | 9/2005 | Kurc |
| 6,969,373 B2 | 11/2005 | Schwartz et al. |
| 7,008,381 B2 | 3/2006 | Janssens |
| 7,008,383 B1 | 3/2006 | Damadian et al. |
| 7,008,394 B2 | 3/2006 | Geise et al. |
| 7,025,732 B2 | 4/2006 | Thompson et al. |
| 7,063,672 B2 | 6/2006 | Schramm |
| 7,137,985 B2 | 11/2006 | Jahng |
| 7,207,949 B2 | 4/2007 | Miles et al. |
| 7,226,450 B2 | 6/2007 | Athanasiou et al. |
| 7,229,401 B2 | 6/2007 | Kindlein |
| 7,670,328 B2 | 3/2010 | Miller |
| 7,699,850 B2 | 4/2010 | Miller |
| 7,811,260 B2 | 10/2010 | Miller et al. |
| 7,815,642 B2 | 10/2010 | Miller |
| 7,850,620 B2 | 12/2010 | Miller et al. |
| 7,951,089 B2 | 5/2011 | Miller |
| 8,038,664 B2 | 10/2011 | Miller et al. |
| 8,419,683 B2 | 4/2013 | Miller et al. |
| 8,480,632 B2 | 7/2013 | Miller et al. |
| 8,506,568 B2 | 8/2013 | Miller |
| 8,641,715 B2 | 2/2014 | Miller |
| 8,656,929 B2 | 2/2014 | Miller et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,812,101 B2 | 8/2014 | Miller et al. |
| 8,974,410 B2 * | 3/2015 | Miller ............... A61M 39/0247 604/116 |
| 10,258,783 B2 * | 4/2019 | Miller .................. A61M 5/158 |
| 11,583,668 B2 * | 2/2023 | Miller .................. A61M 39/0247 |
| 2001/0014439 A1 | 8/2001 | Meller et al. |
| 2001/0047183 A1 | 11/2001 | Privitera et al. |
| 2001/0053888 A1 | 12/2001 | Athanasiou et al. |
| 2002/0020715 A1 | 2/2002 | Gueret |
| 2002/0042581 A1 | 4/2002 | Cervi |
| 2002/0055713 A1 | 5/2002 | Gibbs |

(56) References Cited

U.S. PATENT DOCUMENTS

| | | |
|---|---|---|
| 2002/0120212 A1 | 8/2002 | Ritchart et al. |
| 2002/0138021 A1 | 9/2002 | Pflueger |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van et al. |
| 2003/0195524 A1 | 10/2003 | Barner |
| 2003/0199787 A1 | 10/2003 | Schwindt |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0019297 A1 | 1/2004 | Angel |
| 2004/0019299 A1 | 1/2004 | Ritchart et al. |
| 2004/0034280 A1 | 2/2004 | Privitera et al. |
| 2004/0049128 A1 | 3/2004 | Miller et al. |
| 2004/0064136 A1 | 4/2004 | Papineau et al. |
| 2004/0092946 A1 | 5/2004 | Bagga et al. |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0215102 A1 | 10/2004 | Ikehara et al. |
| 2004/0220497 A1 | 11/2004 | Findlay et al. |
| 2005/0027210 A1 | 2/2005 | Miller |
| 2005/0040060 A1 | 2/2005 | Andersen et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0261693 A1 | 11/2005 | Miller et al. |
| 2005/0267144 A1 | 12/2005 | Mandrea |
| 2006/0011506 A1 | 1/2006 | Riley |
| 2006/0015066 A1 | 1/2006 | Turieo et al. |
| 2006/0036212 A1 | 2/2006 | Miller |
| 2006/0043118 A1 | 3/2006 | Law et al. |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0184063 A1 | 8/2006 | Miller |
| 2006/0189940 A1 | 8/2006 | Kirsch |
| 2007/0016100 A1 | 1/2007 | Miller |
| 2007/0049945 A1 | 3/2007 | Miller |
| 2007/0149920 A1 | 6/2007 | Michels et al. |
| 2007/0213735 A1 | 9/2007 | Saadat et al. |
| 2007/0270775 A1 | 11/2007 | Miller et al. |
| 2008/0015467 A1 | 1/2008 | Miller |
| 2008/0015468 A1 | 1/2008 | Miller |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0119572 A1 | 5/2008 | Owens et al. |
| 2008/0140014 A1 | 6/2008 | Miller et al. |
| 2008/0177200 A1 | 7/2008 | Ikehara et al. |
| 2008/0215056 A1 | 9/2008 | Miller et al. |
| 2008/0221580 A1 | 9/2008 | Miller et al. |
| 2009/0232755 A1 | 9/2009 | Baumann |
| 2011/0082387 A1 | 4/2011 | Miller et al. |
| 2011/0306841 A1 | 12/2011 | Lozman et al. |

FOREIGN PATENT DOCUMENTS

| | | |
|---|---|---|
| CN | 2664675 Y | 12/2004 |
| DE | 10057931 A1 | 8/2002 |
| EP | 0517000 A2 | 12/1992 |
| EP | 0807412 A1 | 11/1997 |
| EP | 1314452 A1 | 5/2003 |
| EP | 1421907 A1 | 5/2004 |
| FR | 0853349 A | 3/1940 |
| FR | 2457105 A1 | 12/1980 |
| FR | 2516386 A1 | 5/1983 |
| GB | 2130890 A | 6/1984 |
| JP | 1052433 A | 2/1989 |
| WO | 93/07819 A2 | 4/1993 |
| WO | 96/31164 A1 | 10/1996 |
| WO | 98/06337 A1 | 2/1998 |
| WO | 98/52638 A2 | 11/1998 |
| WO | 99/18866 A1 | 4/1999 |
| WO | 99/52444 A1 | 10/1999 |
| WO | 00/09024 A1 | 2/2000 |
| WO | 00/56220 A1 | 9/2000 |
| WO | 01/78590 A1 | 10/2001 |
| WO | 2002/041792 A1 | 5/2002 |
| WO | 02/96497 A1 | 12/2002 |
| WO | 03/15637 A1 | 2/2003 |
| WO | 2005/072625 A2 | 8/2005 |
| WO | 2005/110259 A1 | 11/2005 |
| WO | 2005/112800 A2 | 12/2005 |
| WO | 2008/033874 A2 | 3/2008 |
| WO | 2008/081438 A1 | 7/2008 |
| WO | 2011/030573 A1 | 3/2011 |
| WO | 2011/123703 A1 | 10/2011 |

OTHER PUBLICATIONS

Astrom, K. Gunnar, "CT-guided Transsternal Core Biopsy of Anterior Mediastinal Masses," Radiology, vol. 199, 1996, pp. 564-567.

Astrom, K.G., "Automatic Biopsy Instruments Used Through a Coaxial Bone Biopsy System with an Eccentric Drill Tip," Acta Radiological, 1995; 36:237-242.

Australian Exam Report on Patent Application No. 2003240970, 2 pages, Oct. 15, 2007.

Bio.Access.com, Single Use Small Bone Power Tool-How It Works, 1 pg, Jun. 9, 2008.

Buckley et al., "CT-guided bone biopsy: initial experience with commercially available hand held Black and Decker drill," European Journal of Radiology 61:176-180. 2007.

Chinese Office Action with English translation; Application No. 200780000585.5; pp. 15, dated Nov. 19, 2010.

Communication Pursuant to Article 94(3) EPC in European Application No. 05712091.7 dated Apr. 8, 2008.

Communication relating to the results of the partial International Search Report for Mailed PCT/US2005/002484, 6 pages dated May 19, 2005.

Cummings et al.,"ACLS—Principles and Practice" ACLS—The Reference Textbook, American Heart Association, pp. 214-218, 2003.

F .A.S.T. 1 Intraosseous Infusion System with Depth-Control Mechanism Brochure, 6 pages, 2000.

Gunal et al., Compartment Syndrome After Intraosseous Infusion: An Experimental Study in Dogs, Journal od Pediatric Surgery, vol. 31, No. 11, pp. 1491-1493, Nov. 1996.

(56) References Cited

OTHER PUBLICATIONS

Hakan et al., "CT-guided Bone Biopsy Performed by Means of Coaxial Biopsy System with an Eccentric Drill," Radiology, pp. 549-552 (Aug. 1993).
International PCT Search Report and Written Opinion PCT /US2005/ 002484, 15 pages, dated Jul. 22, 2005.
International PCT Search Report and Written Opinion PCT/US2004/ 037753, 16 pages, mailed Jul. 8, 2005.
International PCT Search Report PCT/US03/17167, 8 pages, mailed Sep. 16, 2003.
International PCT Search Report PCT/US03/17203, 8 pages, dated Sep. 16, 2003.
International PCT Search Report PCT/US2004/037753, 6 pages, dated Apr. 19, 2005.
International Prelimarinary Report on Patentability in International Application No. PCT/US2012/046294 dated Jan. 23, 2014.
International Preliminary Report on Patent ability in International Application No. PCT/US2005/002484 dated Aug. 3, 2006.
International Preliminary Report on Patentability for international application PCT/US2006/025201, dated Feb. 7, 2008.
International Preliminary Report on Patentability for international application PCT/US2007/072202. dated Jan. 15, 2009.
International Preliminary Report on Patentability in International Application No. PCT/US/2007/072209, dated May 14, 2009.
International Preliminary Report on Patentability in International Application No. PCT/US2007/072217 dated Feb. 12, 2009.
International Search Report and Written Opinion for international application PCT/US2007/078203, dated May 13, 2008.
International Search Report and Written Opinion for international application PCT/US2007/078204, dated May 15, 2008.
International Search Report and Written Opinion for international application PCT/US2007/078205, dated Sep. 11, 2007.
International Search Report and Written Opinion for international application PCT/US2007/078207, dated Apr. 7, 2008.
International Search Report and Written Opinion for international application PCT/US2008/0500346. dated May 22, 2008.
International Search Report and Written Opinion for International Patent Application No. PCT/US2007/072202, dated Mar. 25, 2008.
International Search Report and Written Opinion issued in PCT Application No. PCT/US2007/072209 dated Apr. 25, 2008.
International Search Report and Written Opinion issued in PCT Application No. PCT/US2007/072217 dated Mar. 31, 2008.
International Search Report and Written Opinion, PCT/US08/52943 8 pages, Mailing Date Sep. 26, 2008.
International Search Report in International Application No. PCT/ US2012/046294 dated Jan. 24, 2013.
Liakat A. Parapia, "Trepanning or trephines: a history of bone marrow biopsy," British Journal of Haematology, pp. 14-19 (2007).
Michael Totty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages (2008).
Non-Final Office Action, U.S. Appl. No. 10/449,476, 8 pages, dated Oct. 29, 2008.
Notice of Allowance in U.S. Appl. No. 11/620,927 mailed Jun. 3, 2014.
Notice of Allowance in U.S. Appl. No. 12/407,651 mailed Jun. 11, 2014.
Notification of the First Chinese Office Action, Application No. 200580003261.8, 3 pages, dated Mar. 21, 2008.
Office Action for European application 03731475.4, dated Oct. 11, 2007.
Office Action for U.S. Appl. No. 11/427,501, dated Aug. 7, 2008.
Office Action in Chinese Patent Application No. 200780000585.5 dated Feb. 29, 2012.
Office Action in Chinese Patent Application No. 200780000585.5 dated Jan. 21, 2013.
Office Action in Chinese Patent Application No. 200780000585.5 dated Sep. 26, 2012.
Office Action in European Application No. 03756317.8 dated Dec. 28, 2006.
Office Action in European Application No. 08158699.2 dated Nov. 4, 2008.
Office Action in European Application No. 1281109035 dated Feb. 20, 2014.
Office Action in Taiwanese Patent Application No. 096140082 dated Jun. 5, 2014.
Office Action in Taiwanese Patent Application No. 096140082 dated Oct. 30, 2013.
Office Action in U.S. Appl. No. 13/546,894 dated Dec. 30, 2013.
Office Action in U.S. Appl. No. 13/546,894 dated Jul. 18, 2014.
Office Communication issued in European Patent Application No. 09150973.7, dated Dec. 22, 2011.
Office Communication issued in Taiwanese Patent Application No. 096140082, dated Mar. 27, 2013.
PCT Invitation to Pay Additional Fees in International Application No. PCT/US2007/072209 dated Dec. 3, 2007.
Pediatric Emergency, Intraosseous Infusion for Administration of Fluids and Drugs, www.cookgroup.com, 1 pg (2000).
Pediatrics, "2005 American Heart Association Guidelines for Cardiopulmonary Resuscitation and Emergency Cardiovascular Care of Pediatric and Neonatal Patients: Pediatric Advanced Life Support," Official Journal of the American Academy of Pediatrics. Downloaded from www.pediatrics.org on Feb. 21, 2007.
Rejection Decision in Chinese Patent Application No. 200780000585.5 dated Apr. 27, 2013.
Riley, et al., "A Pathologists Perspective on Bone Marrow Aspiration Biopsy: Performing a Bone Marrow Examination" J Clin Lab Analysis. 18:70-90, 2004.
Search Report and Written Opinion in International Application No. PCT/US2006/025201 dated Jan. 29, 2007.
Search Report in European Application No. 08158699.2 dated Aug. 2008.

\* cited by examiner

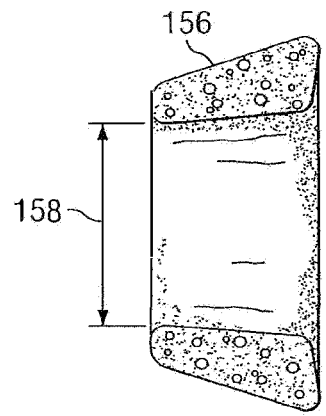
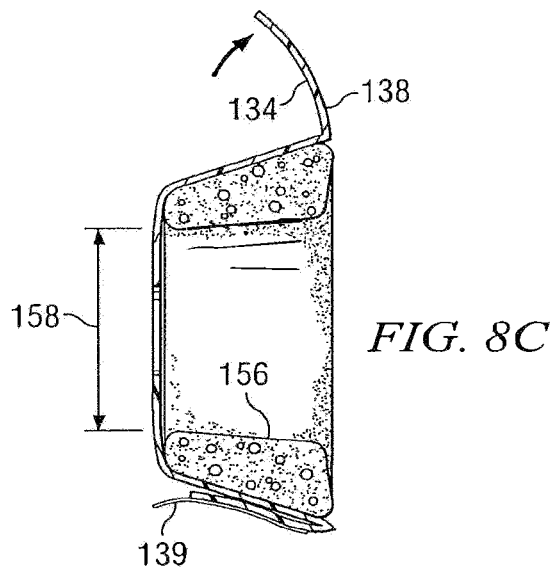
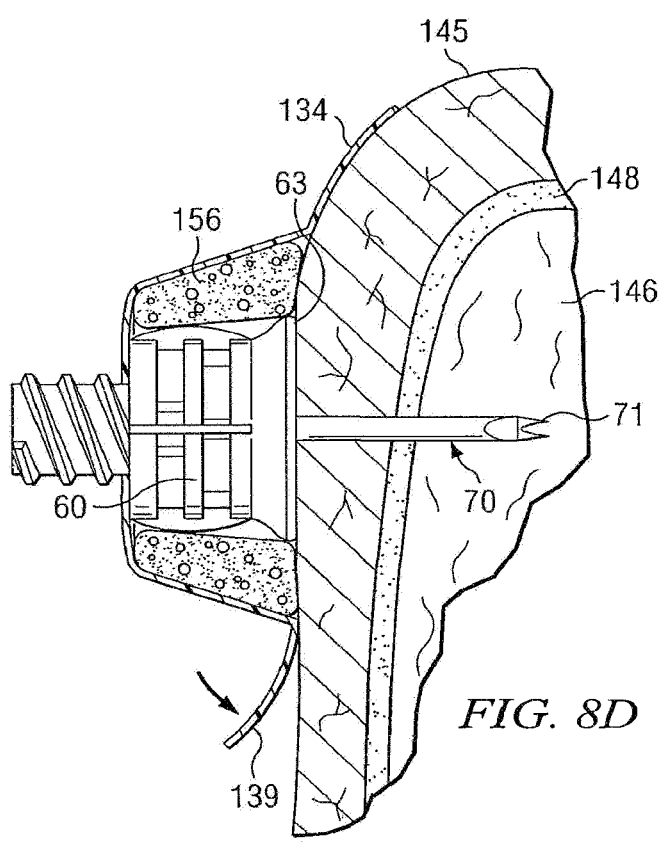

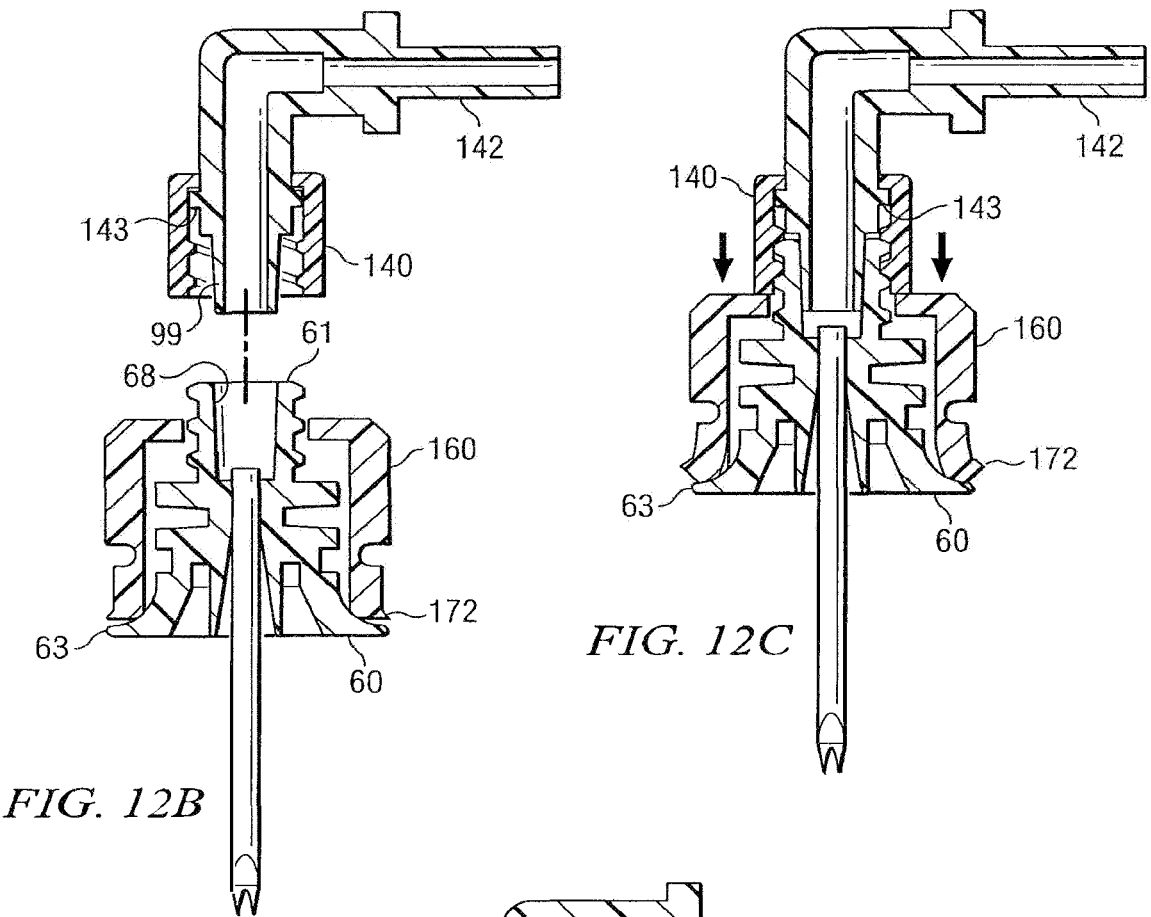
FIG. 12B
FIG. 12C
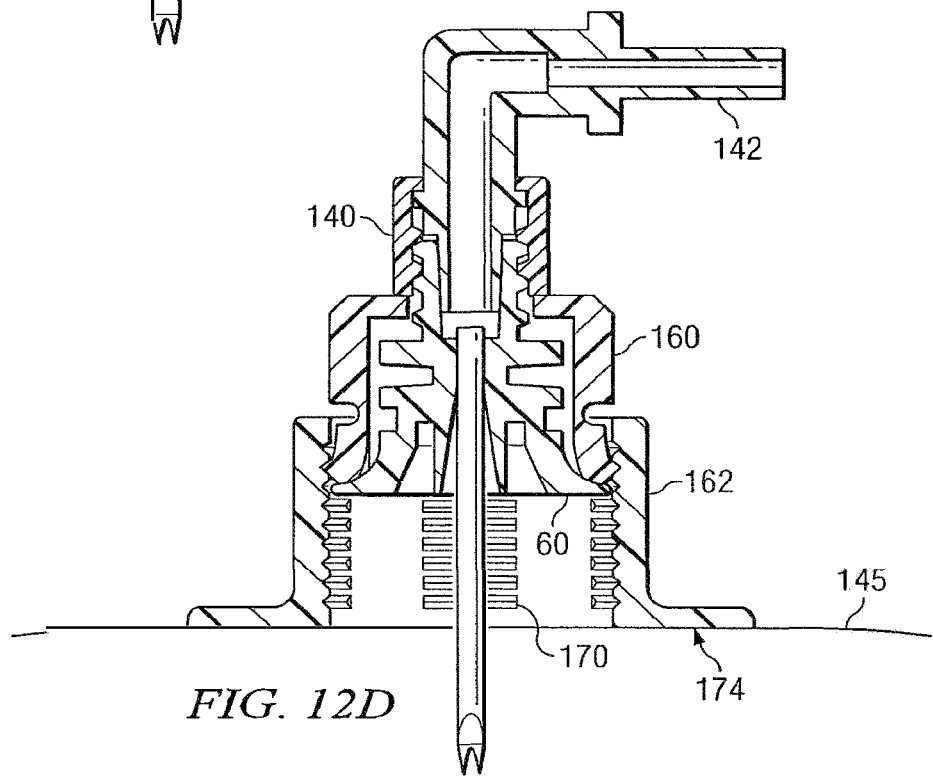
FIG. 12D

APPARATUS AND METHODS TO COMMUNICATE FLUIDS AND/OR SUPPORT INTRAOSSEOUS DEVICES

RELATED APPLICATIONS

This application is a divisional application of U.S. patent application Ser. No. 16/372,056, filed Apr. 1, 2019, which is a divisional application of U.S. patent application Ser. No. 14/643,839, filed Mar. 10, 2015, now U.S. Pat. No. 10,258,783, which is a continuation application of U.S. patent application Ser. No. 11/619,390, filed Jan. 3, 2007, now U.S. Pat. No. 8,974,410, which claims the benefit of U.S. Provisional Patent Application Ser. No. 60/863,521, filed Oct. 30, 2006. The contents of each of these applications are incorporated herein by reference in their entirety.

TECHNICAL FIELD

The present disclosure is related to apparatus and methods which may be used to support an intraosseous device after insertion into a target area and/or to communicate fluids with the target area via the intraosseous device.

BACKGROUND OF THE DISCLOSURE

Vascular access is often essential to viability of a patient in emergency situations, during transportation to a medical facility and during treatment at the medical facility. Obtaining vascular access may be a significant problem in five to ten percent of patients of all ages and weight in pre-hospital and hospital environments. This equates to approximately six (6) million patients in the U.S. annually. For example patients suffering from conditions such as shock, cardiac arrest, drug overdose, dehydration, diabetic coma, renal failure and altered states of consciousness may have very few (if any) accessible veins.

In a hospital or similar medical facility, central line access is often an alternative to IV access. However, central line access generally takes longer, costs more, may have a higher risk of complications and requires skilled personnel to properly insert the central line. In many hospital environments, nurses and physicians are increasingly turning to intraosseous (IO) access as an alternative to IV access, rather than central lines. In pre-hospital environments, paramedics and other emergency medical service (EMS) providers are often finding that IO access may be quick, safe and effective when IV placement is challenging.

Intraosseous (IO) access to bone and associated bone marrow has been used for other procedures including, but not limited to, obtaining biopsy specimens for analysis and research and also for bone marrow transplantation and/or stem cell research.

SUMMARY OF THE DISCLOSURE

In accordance with teachings of the present disclosure, apparatus and methods may be provided to facilitate access to a patient's vascular system and to communicate fluids with the vascular system. Intraosseous (IO) devices and techniques incorporating teachings of the present disclosure may communicate various fluids including, but not limited to, drugs and medication with the vascular system. Supporting structures, attachment devices and attachment techniques incorporating teachings of the present disclosure may be used to enhance performance of various types of IO devices including, but not limited to, IO devices used to communicate fluids with the vascular system and/or IO devices used to obtain bone and/or bone marrow samples.

One aspect of the present disclosure may include providing apparatus and methods for stabilizing or securing an intraosseous device disposed in a bone and associated bone marrow. Supporting structures, attachment devices and attachment techniques incorporating teachings of the present disclosure may be used with a wide variety of intraosseous devices.

The present disclosure may provide apparatus and methods to establish vascular access during treatment at a wide variety of acute and chronic conditions at locations and facilities including, but not limited to, accident sites, emergency rooms, battlefields, emergency medical services (EMS) facilities, oncology treatment centers, and chronic disease treatment facilities. Various teachings of the present disclosure may be used during treatment of animals in a veterinary practice.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 5E is a schematic drawing showing injection of fluids into a connector assembly in accordance with teaching of the present disclosure;

FIG. 6A is a schematic drawing showing a top plan view of one embodiment of a supporting structure and attachment mechanism according to the present disclosure;

FIG. 6B is a schematic drawing showing a bottom plan view of the supporting structure and attachment mechanism shown in FIG. 6A;

FIG. 8B is a schematic drawing in section showing one component of one embodiment of a supporting structure for an intraosseous device incorporating teachings of the present disclosure;

FIG. 8C is a schematic drawing in section showing multiple components of one embodiment of a supporting structure for an intraosseous device in accordance with teaching of the present disclosure;

FIG. 8D is a schematic drawing in section taken along line 8B-8B of FIG. 8A with portions broken away showing an intraosseous device and the supporting structure of FIG. 8C installed at an insertion site;

FIG. 12B is a schematic drawing in section showing the embodiment of FIG. 12A with the support structure partially assembled;

FIG. 12C is a schematic drawing in section showing the embodiment of FIG. 12A with the support structure partially assembled; and FIG. 12D is a schematic drawing in section showing the embodiment of FIG. 12A with the support structure partially assembled.

DETAILED DESCRIPTION OF THE DISCLOSURE

Figure 1:
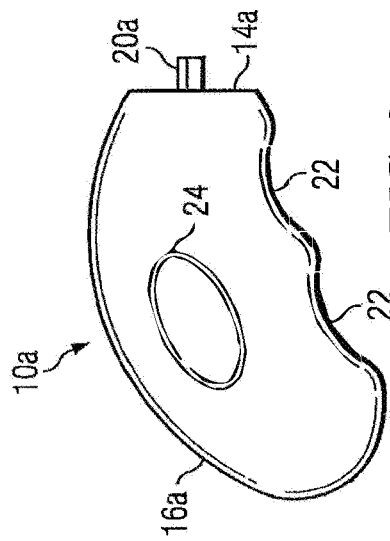
FIG. 1 is a schematic drawing showing an isometric view of a powered driver which may be used to place an intraosseous device at a selected insertion site.

Preferred embodiments of the disclosure and its advantages are best understood by reference to FIGS. 1-12D wherein like numbers refer to same and like parts.

Vascular system access may be essential for treatment of many serious diseases, chronic conditions and acute emergency situations. Yet, many patients experience extreme difficulty obtaining effective treatment because of inability to obtain or maintain intravenous (IV) access. An intraosseous (IO) space provides a direct conduit to a patent's vascular system and systemic circulation. Therefore, IO access is an effective route to administer a wide variety of drugs, other medications and fluids. Rapid IO access offers great promise for almost any serious emergency that requires vascular access to administer life saving drugs, other medications and/or fluids when traditional IV access is difficult or impossible.

The upper tibia proximate a patient's knee or the humeral head proximate a patient's shoulder may be used as insertion sites for an IO device to establish access with the patient's vascular system. Sternal access (not expressly shown) may also be used as an insertion site. Availability of multiple intraosseous sites has proven to be especially important in applications such as emergency treatment of battlefield casualties or other mass casualty situation. Teachings of the present disclosure may be used at a wide variety of insertion sites.

The humeral head and sternum provide insertion sites for an intraosseous device located above the diaphragm of a patient. Placing or inserting an intraosseous device above the diaphragm may be preferred by some emergency room physicians and trauma surgeons for rapid vascular access.

Teachings of the present disclosure may be satisfactorily used to place or insert an intraosseous device and to communicate fluids with the intraosseous device at a wide variety of locations. Teachings of the present disclosure are not limited to IO devices which may only be inserted at the tibia, humerus, or sternum.

Intraosseous access may also be used as a "routine" procedure with chronic conditions which substantially reduce or eliminate the availability of conventional IV sites. Examples of such chronic conditions may include, but are not limited to, dialysis patients, seriously ill patients in intensive care units and epilepsy patients. Intraosseous devices along with supporting structure and/or monitoring equipment incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description.

The ability to satisfactorily maintain an intraosseous (IO) device such as an IO needle at a desired insertion site may be problematic when a patient is moving or has the potential to move. Inserting an IO device in the wrong place may expose a patient to potential harm. Patient movement may be of special concern for patients suffering from status epilepticus or violent patients (drug overdoses or mental status changes) that need to be controlled for their safety and treatment. Epileptic patients may shake violently for prolonged periods which makes starting a conventional IV nearly impossible.

Insertion sites and associated target areas for IO placement such as a patient's tibia, humerus, or sternum are often larger than insertion sites and associated target areas for placement of an IV device making IO insertion easier than IV insertion. Problems with maintaining an IO device may be minimized by using supporting structures along with attachment mechanisms and attachment techniques incorporating teachings of the present disclosure. Such supporting structures, attachment mechanisms and attachment techniques may be easy to apply, even in difficult field environments.

Supporting structures, attachment mechanisms and attachment techniques may also be used when harvesting bone and/or bone marrow samples using an intraosseous device. Such supporting structures, attachment mechanisms and attendant techniques may be particularly useful when an IO device is inserted into a patient's humeral head or sternum (not expressly shown) or when inserted into small or pediatric patients. Such supporting structures, attachment mechanisms, and/or attachment techniques may substantially reduce and/or eliminate wobble which may occur during manipulation of an intraosseous device during treatment to obtain one or more samples at a respective insertion site. In addition, such attachment mechanisms and techniques may substantially reduce and/or eliminate the chance of dislodging the IO device in the event of patient movement or inadvertent contact by other persons.

The term "driver" may be used in this application to include any type of powered driver or manual driver satisfactory for installing an intraosseous (TO) device such as a penetrator assembly or an IO needle into a selected target site.

For some applications a powered driver or a manual driver may be directly coupled with an IO device. For other applications various types of connectors may be used to couple a manual driver or a powered driver with an IO device. A wide variety of connectors and associated connector receptacles, fittings and/or other types of connections with various dimensions and configurations may be satisfactorily used to releasably engage an IO device with a powered driver or a manual driver.

The term "intraosseous (IO) device" may be used in this application to include any hollow needle, hollow drill bit, penetrator assembly, bone penetrator, catheter, cannula, trocar, inner penetrator, outer penetrator, IO needle or IO needle set operable to provide access to an intraosseous space or interior portions of a bone. A wide variety of trocars, spindles and/or shafts may be disposed within a cannula during installation at a selected target area. Such trocars, spindles and shafts may also be characterized as inner penetrators. A cannula may be characterized as an outer penetrator.

The term "fluid" may be used within this patent application to include any liquid including, but not limited to, blood, water, saline solutions, IV solutions, plasma or any mixture of liquids, particulate matter, dissolved medication and/or drugs appropriate for injection into bone marrow or other target sites. The term "fluid" may also be used within this patent application to include body fluids such as, but not limited to, blood, bone marrow and cells which may be withdrawn from a target site.

Various features of the present disclosure may be described with respect to powered driver 10 and/or manual driver 10a. Various features of the present disclosure may also be described with respect to intraosseous device-hub 60. However, supporting structures, attachment mechanisms and attachment techniques incorporating teachings of the present disclosure may be satisfactorily used with a wide variety of drivers and intraosseous devices. The present disclosure is not limited to use with intraosseous device-hub 60 or drivers 10 or 10a.

FIG. 1 shows an embodiment of a powered driver 10 which may be satisfactorily used to insert intraosseous needle set 40 into a selected target area or penetration site. Powered driver 10 may include housing 12 with various types of motors and/or gear assemblies disposed therein (not expressly shown). A rotatable shaft (not expressly shown) may be disposed within housing 12 and connected with a gear assembly (not expressly shown). Various types of fittings, connections, connectors and/or connector receptacles may be provided at one end of the rotatable shaft extending from end 14 of housing 12.

For some applications pin type fitting or connector 20 may be formed on the one end of the rotatable shaft. A matching box type fitting or connector receptacle may be provided on an intraosseous device so that connector 20 of powered driver 10 may be releasably engaged with the intraosseous device. For some applications, connector 20 may have a pentagonal shaped cross section with tapered surfaces formed on the exterior thereof.

Handle 16 may include a battery (not expressly shown) or other power source. Handle 16 may also include trigger assembly 17 for use in activating powered driver 10. Examples of powered drivers are shown in pending patent application Ser. No. 10/449,503 filed May 30, 2003 entitled "Apparatus and Method to Provide Emergency Access to Bone Marrow," now U.S. Pat. No. 7,670,328; Ser. No. 10/449,476 filed May 30, 2003 entitled "Apparatus and Method to Access Bone Marrow," now U.S. Pat. No. 7,699,850; and Ser. No. 11/042,912 filed Jan. 25, 2005 entitled "Manual Intraosseous Device," now U.S. Pat. No. 8,641,715.

Figure 2:
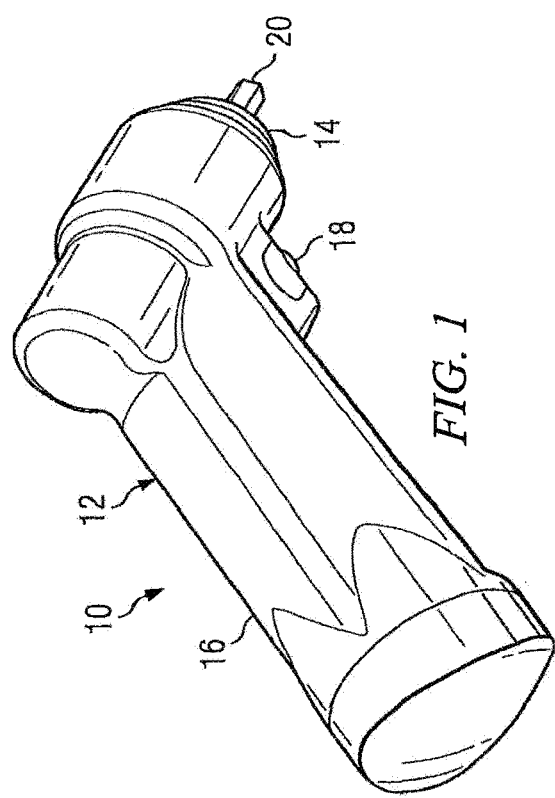
FIG. 2 is a schematic drawing showing a side view of a manual driver which may be used to place an intraosseous device at a selected insertion site.

FIG. 2 shows one example of a manual driver which may be satisfactorily used to insert an intraosseous device into a selected target area. For this embodiment manual driver 10a may be generally described as having handle 16a with a "pistol grip" configuration. Handle 16a has an ergonomic design with finger grips 22 and one or more finger rests 24.

Connector 20a may extend from first end 14a of handle 16a. Connector 20a may have a configuration and dimensions similar to previously described connector 20. However, manual drivers may be provided with a wide variety of connectors and/or connector receptacles. Various details concerning manual drivers are discussed in more detail in pending U.S. patent application, Ser. No. 11/042,912 filed Jan. 25, 2005, entitled "Manual Intraosseous Device," now U.S. Pat. No. 8,641,715.

Figure 3:
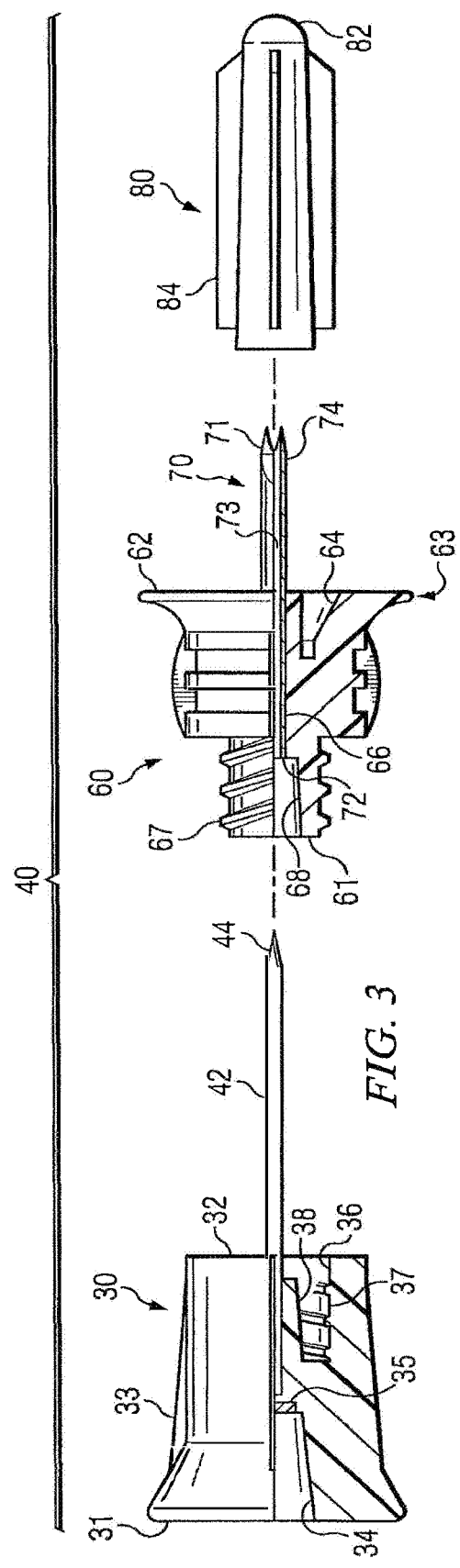
FIG. 3 is a schematic drawing in section and in elevation with portions broken away showing an exploded view of one example of an intraosseous device.

FIG. 3 is a schematic drawing showing an exploded view of one example of a penetrator assembly which may be used to provide access to a patient's vascular system. Penetrator assembly or IO needle set 40 may include connector 30, hub 60 and cover 80. Connector 30 may be described as having a generally cylindrical configuration defined in part by first end 31 and second end 32.

First end 31 may include opening 34 formed with various configurations and/or dimensions. For some applications opening 34 may be sized to receive portions of a drive shaft. One or more webs (not expressly shown) may also be formed in first end 31 extending from opening 34. Open segments or void spaces (not expressly shown) may be formed between such webs. Opening 34 and associated webs (if any) may be used to releasably engage connector 30 with either a manual driver or a powered driver.

The configuration and dimensions of opening 34 may be selected to be compatible with releasably engaging connector 30 of needle set 40 with connector 20 of powered driver 10 or connector 20a of manual driver 10a. For some applications metallic disk 35 may be disposed within opening 34 for use in releasably engaging needle set 40 with a magnet (not expressly shown) disposed on the end of connector 20 or 20a.

For some applications exterior portion of connector 30 may include an enlarged tapered portion adjacent to first end 31. A plurality of longitudinal ridges 33 may also be formed on the exterior of connector 30 proximate first end 31. The enlarged tapered portion and/or longitudinal ridges 33 may allow an operator to grasp associated needle set 40 during attachment with a driver and may facilitate disengagement of connector 30 from hub 60 after outer penetrator or cannula 70 has been inserted into a bone and associated bone marrow.

Second opening 36 may be formed in second end 32 of connector 30. For example threads 37 may be formed on interior portions of opening 36 extending from second end 32. Threads 37 may be sized to engage threads 67 formed on an exterior portion of hub 60. In addition, opening 36 may include male luer slip 38, configured to correspond to female luer slip 68 in hub 60. It should be noted that male luer slip 38 and female luer slip 68 do not come into physical contact when connector 30 and hub 60 are connected. Threads 37 and 67 may be characterized as forming portions of a Luer lock connection. However, the present disclosure is not limited to threads 37 and 67. Various types of releasable connections including, but not limited to, other types of locking connections may be formed on adjacent portions of connector 30 and hub 60.

Trocar or inner penetrator 42 may be securely engaged with connector 30 extending from second end 32. The dimensions and configuration of inner penetrator 42 may be selected to allow inner penetrator 42 to be slidably inserted into longitudinal bore 73 of outer penetrator or cannula 70. Trocar 42 may include first end or tip 44. The dimensions and configuration of tip 44 may be selected to accommodate inserting penetrator assembly 40 into bone and associated bone marrow at a selected target area in a patient.

Hub 60 may include first end or distal end 61 and second end or proximal end 62. First end 61 of hub 60 may have a generally cylindrical pin-type configuration compatible with releasably engaging hub 60 with second end 32 of connector 30. As previously noted, threads 67 formed adjacent to first end 61 of hub 60 may be releasably engaged with threads 37 formed on interior portions of opening 36 of connector 30.

For some applications first end 61 of hub 60 may be configured to accommodate various connectors and/or to allow access for various methods of fluid delivery (e.g., a luer lock, a syringe, a standard IV connection and/or a needle). For example, first end 61 of hub 60 may include a check valve (not expressly shown), the check valve operable to allow fluid access via engaged luer lock connections and to restrict fluid access in the absence of an engaged luer lock connector. In another example, first end 61 of hub 60 may include a gasket (not expressly shown) operable to allow fluid access when punctured by a needle and to restrict fluid access in the absence of an engaged needle.

For some applications second end 62 of hub 60 may include flange 63. The dimensions and configuration of second end 62 of hub 60 may be varied to accommodate various insertion sites for an IO device. Hub 60 may be formed with a wide variety of flanges or other configurations compatible with contacting a patient's skin adjacent a desired insertion site.

Passageway 66 may extend from first end 61 through hub 60 to second end 62. Portions of passageway 66 extending from second end 62 may have dimensions selected to be compatible with securely engaging exterior portions of outer penetrator or cannula 70 with hub 60. Second end 72 of cannula 70 may be disposed within passageway 66 between first end 61 and second end 62. First end 71 of cannula 70 may extend from second end 62 of hub 60. Portions of passageway 66 extending from first end 61 of hub 60 may have an enlarged inside diameter to accommodate attachment with various types of fluid connectors.

Cannula or outer penetrator 70 may have longitudinal bore 73 extending from first end 71 to second end 72. Exterior dimensions of trocar or inner penetrator 42 are preferably selected to allow inner penetrator 42 be inserted through outer penetrator 70 with first end 44 of inner penetrator 42 generally aligned with first end 71 of outer penetrator 70 after threads 67 have been engaged with threads 37.

Tip 71 of outer penetrator 70 and/or tip 44 of inner penetrator 42 may be operable to penetrate bone and associated bone marrow. The configuration of tips 71 and 44 may be selected to penetrate a bone, bone marrow and other portions of a patient's body with minimum trauma. For some applications tip 44 of inner penetrator 42 may have a generally trapezoid shape with one or more cutting surfaces.

For some applications tips 71 and 44 may be ground together as a single unit during an associated manufacturing process. Providing a matching fit allows respective tips 71 and 44 to act as a single drilling unit to minimize damage as portions of IO needle set 40 are inserted into a bone and associated bone marrow.

Inner penetrator 42 may sometimes include a longitudinal groove (not expressly shown) that runs along one side of inner penetrator 42 to allow bone chips and/or tissue to exit an insertion site as penetrator assembly 40 is drilled deeper into an associated bone. Outer penetrator 70 and/or inner penetrator 42 may be formed from various materials including, but not limited to, stainless steel, titanium or any other material having suitable strength and durability to penetrate bone and associated bone marrow. The combination of hub 60 with cannula 70 may sometimes be referred to as an "intraosseous needle." The combination of trocar 42 with cannula 70 may sometimes be referred to as a "penetrator set."

Second end 62 and particularly flange 63 may be used to stabilize hub 60 after insertion into a selected target area of a patient. Second end 32 of connector 30 may be releasably engaged from first end 61 of hub 60 after insertion of outer penetrator 70 into associated bone marrow. The depth of such insertion may be dependent upon the distance between tip 71 of cannula 70 and second end 62 of hub 60. Various types of tubing and/or conduit may then be engaged with threads 67 formed on the exterior of hub 60 proximate first end or pin end 61.

Annular slot or groove 64 may be formed within second end 62 and sized to receive one end of protective cover or needle cap 80. Slot or groove 64 may be used to releasably engage cover 80 with penetrator assembly 40. For some applications cover 80 may be described as a generally hollow tube having rounded end or closed end 82. Cover 80 may be disposed within annular groove 74 to protect portions of outer penetrator 70 and inner penetrator 42 prior to attachment with a manual driver or a powered driver. Cover 80 may include a plurality of longitudinal ridges 84 formed on the exterior thereof. Longitudinal ridges 84 may cooperate with each other to allow installing and removing cover or needle cap 80 without contaminating portions of an associated penetrator needle or IO device. Cover 80 may be formed from various types of plastics and/or metals.

Figure 4:
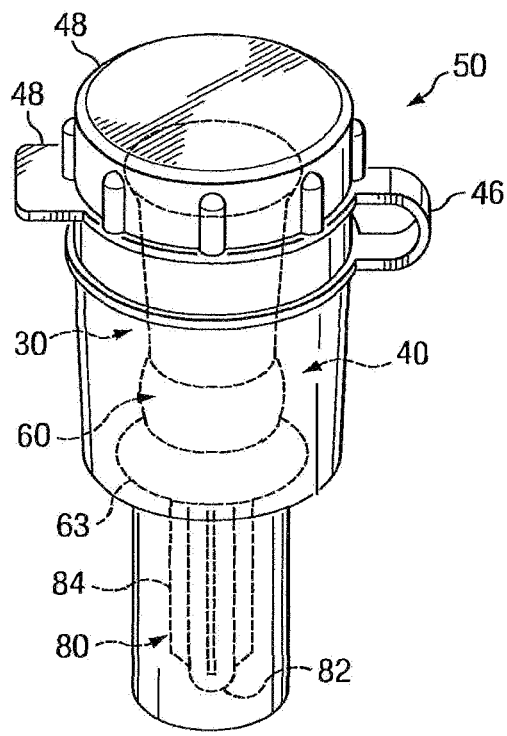
FIG. 4 is a schematic drawing showing an isometric view of the intraosseous device of FIG. 3 disposed in a container.

Container 50 as shown in FIG. 4 may include lid 48. Lid 48 may be configured to allow lid 48 to be flipped open with one or more digits of an operator's hand. With lid 48 open, an operator may releasably engage a driver with an IO device disposed in container. For example, connector 20 of powered driver 10 may be releasably engaged with connector receptacle 34 of IO needle set 40. Flexible connector 46 may be used to retain lid 48 with container 50 after lid 48 has been opened.

Figure 7A:
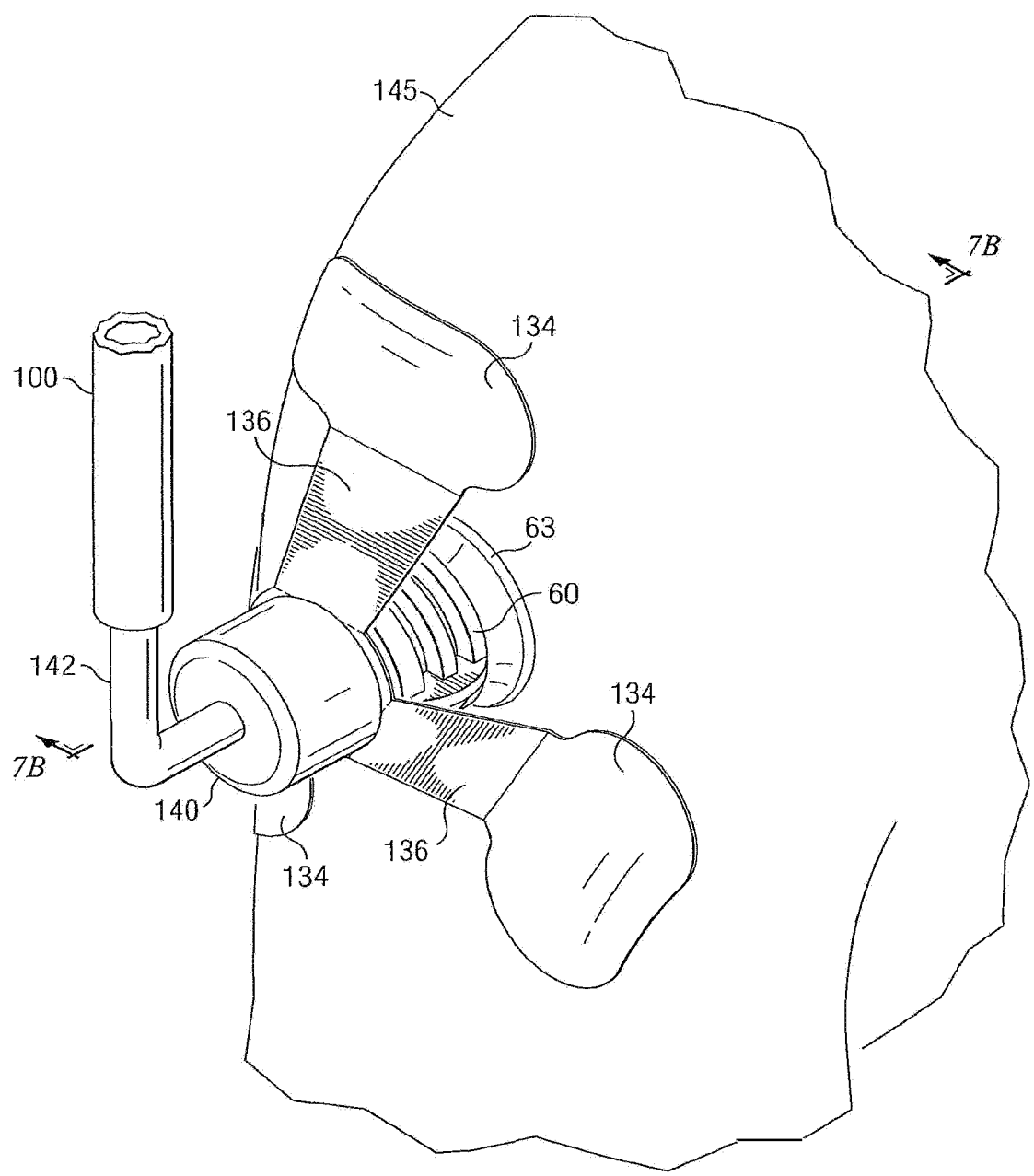
FIG. 7A is a drawing showing an isometric view with portions broken away of a supporting structure and attachment mechanism installed at an insertion site according to one embodiment of the current disclosure.
Figure 7B:
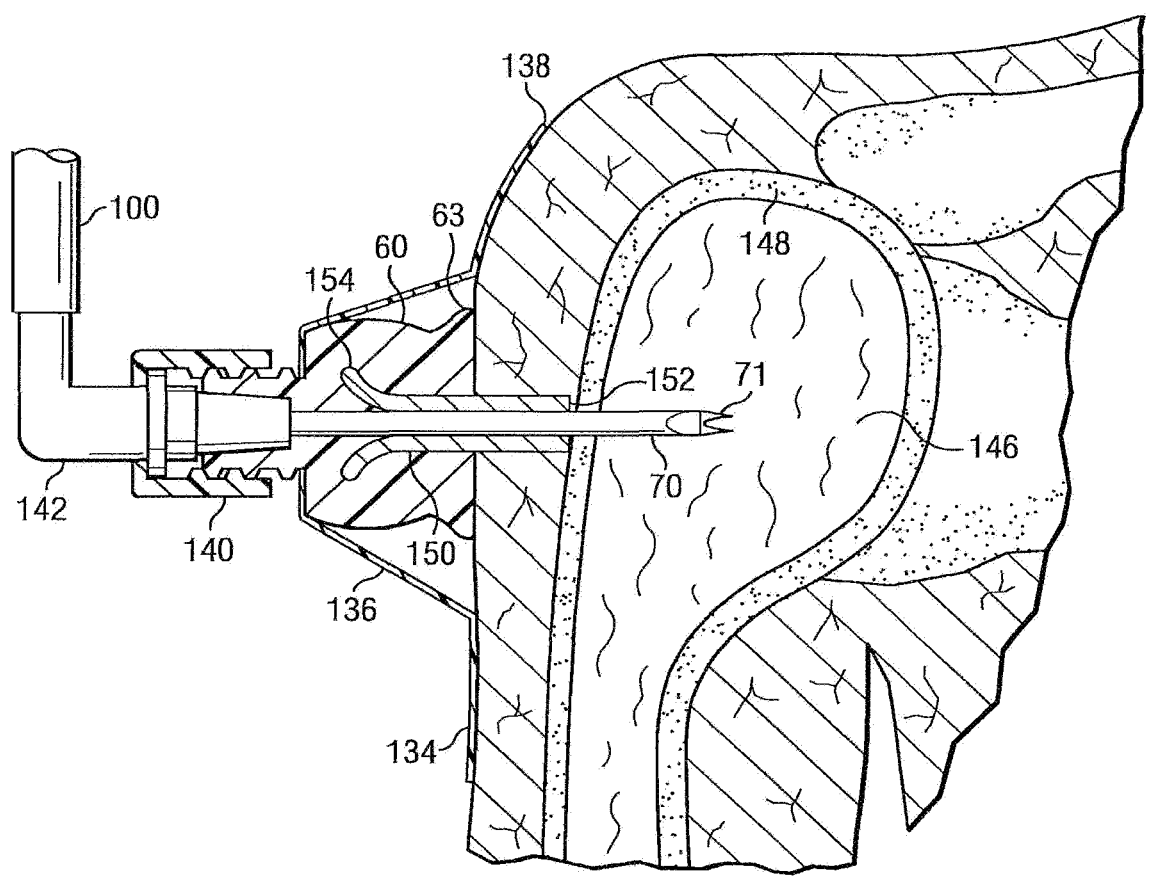
FIG. 7B is a schematic drawing in section taken along line 7B-7B of FIG. 7A showing an intraosseous device inserted into a bone and associated bone marrow along with a supporting structure and attachment mechanism incorporating teachings of the present disclosure.

Various examples of apparatus and methods which may be used to communicate fluids with an intraosseous device in accordance with teachings of the present disclosure are shown in FIGS. 5A-5E. Various examples of supporting structures, supporting devices, attachment mechanisms and attachment techniques incorporating teachings of the present disclosure are shown in FIGS. 6A-11C. Various features of the present disclosure may also be discussed with respect to bone 148 and associated bone marrow 146 as shown in FIGS. 7B and 8D. Bone 148 and bone marrow 146 may be representative of a portion of a patient's upper arm or humeral head.

FIGS. 5A-5E show several embodiments of devices for allowing fluid communication to various types of connections including, but not limited to, a conventional Luer lock connection (not expressly shown) associated with supplying IV fluids and/or medications to a patient.

Figure 5A:
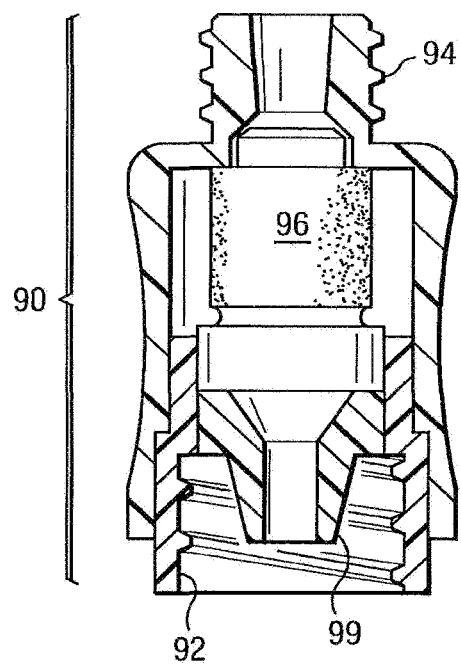
FIG. 5A is a schematic drawing showing an isometric view of an apparatus which may be used to communicate fluids with a target area via an intraosseous device in accordance with teachings of the present disclosure.

For example, FIG. 5A shows one example of connector assembly 90 which may be used to attach tubing or other devices with an intraosseous device in accordance with teachings of the present disclosure. Connector assembly 90 may include any appropriate features or components selected to be compatible with external features of hub 60 or tubing extending therefrom. In some embodiments, such as that shown in FIG. 5A, connector assembly 90 may include internal threads 92 selected to be compatible with threads 67 disposed on hub 60.

Connector assembly 90 may also include any appropriate features or components selected to facilitate attachment to any suitable connections (e.g., extension tubes) for fluid delivery or monitoring devices. For example, connector assembly 90 may include external threads 94 selected to be compatible with a luer lock or other threaded connection.

Connector assembly 90 may include components intended to allow fluid access to hub 60 when appropriate connectors are present. For example, connector assembly may include plug 96. Plug 96 may be any compressible material (e.g., rubber and/or synthetic rubber). In such embodiments, connector assembly 90 may be configured so that plug 96 is under at least some compression in order to create a liquid seal against an inner surface of connector assembly 90. For example connector assembly 90 may include a Halkey-Roberts luer activated valve.

Figure 5B:
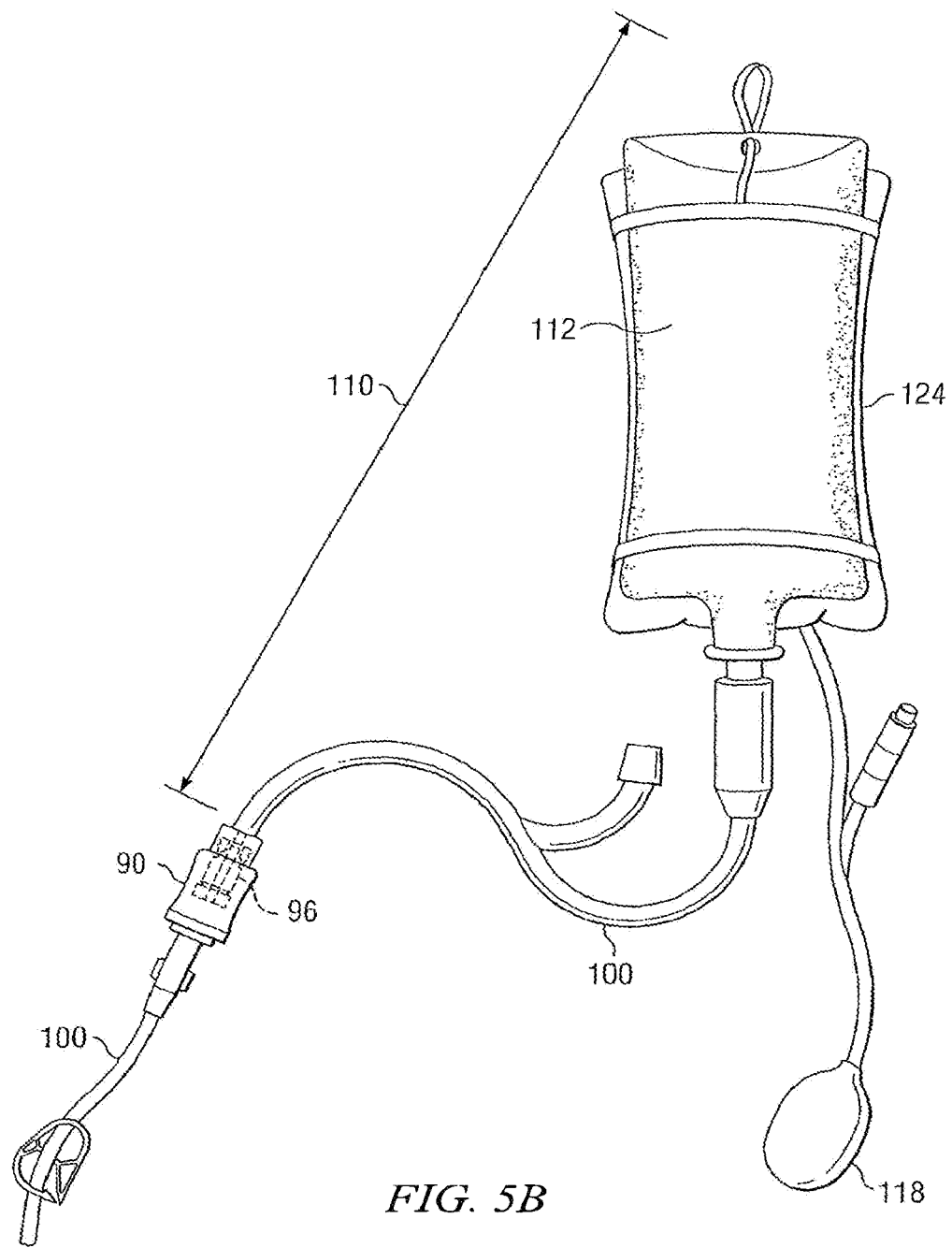
FIG. 5B is a schematic drawing in section showing one example of a connector assembly which may be used to attach a fluid source, pressure pump, and tubing with an intraosseous device in accordance with teachings of the present disclosure.

FIG. 5B shows an apparatus which may be used to communicate fluids with a target area via an intraosseous device in accordance with teachings of the present disclosure. In some embodiments, such as that shown in FIG. 5B, the apparatus may include traditional IV fluid equipment 110. In such embodiments, connecting bag 112 to connector assembly 90 may include compressing plug 96 allowing fluid communication with the interior of connector assembly 90. Compressing plug 96 allows fluid to pass through flexible tubing 100 and thus to hub 60.

One having ordinary skill in the art may recognize additional traditional medical equipment that may be compatible with the I0 devices described herein. Intraosseous infusion may often require a higher pressure than that normally used for intraosseous infusion. For embodiments such as shown in FIG. 5B, fluid bag 112 may be disposed in pressure cuff 124. Bulb 118 and/or another mechanism may be used to control and/or increase the pressure applied to the fluid in bag 112 by pressure cuff 124. In embodiments including pressure cuff 124 and bulb 118, bulb 118 may be operable to inflate pressure cuff 124 through manual and/or automatic compression. In an alternative embodiment, a pressure pump or other mechanism (not expressly shown) may be used to control and/or increase the pressure of fluid supplied to connector assembly 90. Pressure cuff 124 may be any device or apparatus configured to apply pressure to bag 112, thereby increasing the pressure of any fluid contained in bag 112.

Figure 5C:
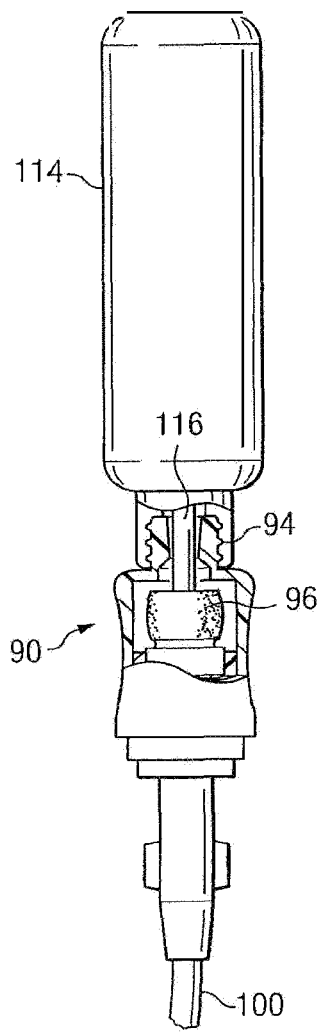
FIG. 5C is a schematic drawing with portions broken away showing one example of an ampule which may be connected with an intraosseous device in accordance with the teachings of the present disclosure.

FIG. 5C shows one example of an apparatus which may be connected to hub 60 using flexible tubing 100 in accordance with the teachings of the present disclosure. In such embodiments, ampule 114 may be attached to flexible tubing 100 using connector assembly 90 as discussed in more detail as part of FIG. 5B. Flexible tubing 100 may be connected to other components of right angle connector 142 and hub 60 as shown in FIG. 7A. In such embodiments, connecting ampule 114 may include compressing plug 96 allowing fluid communication with the interior of connector assembly 90 and flexible tubing 100. For example, ampule 114 may include a projection configured to extend within the body of connector assembly 90 and make contact with plug 96. In the embodiment shown in FIG. 5C, ampule 114 may include tube 116 configured to compress plug 96 when ampule 114 is threaded onto external threads 94 of connector assembly 90.

Figure 5D:
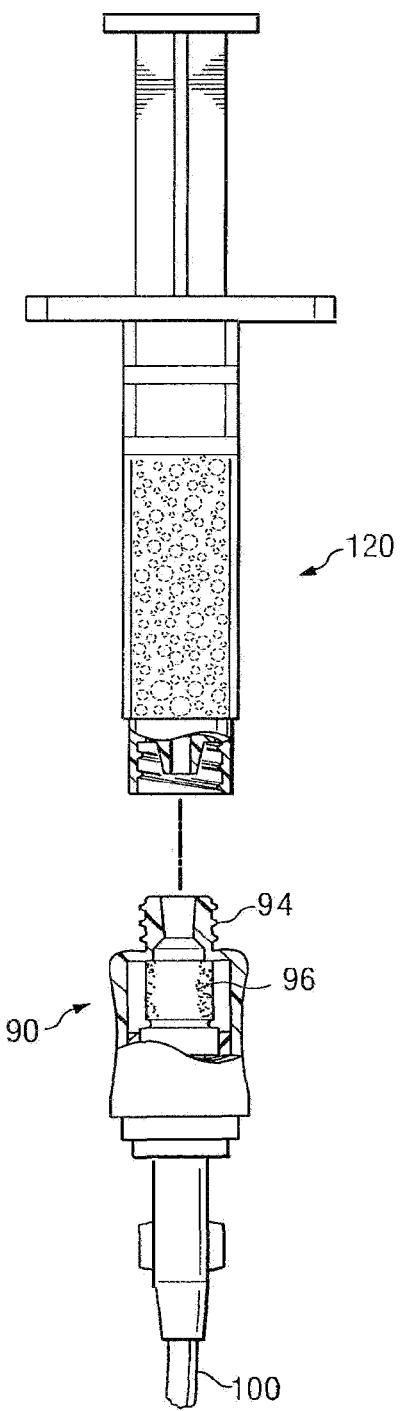
FIG. 5D is a schematic drawing in section and in elevation with portions broken away showing one example of a connector assembly operable for use to inject drugs or medication into an intraosseous device in accordance with teachings of the present disclosure.

FIG. 5D shows fluids contained in hypodermic syringe 120 in preparation for injection into connector assembly 90 coupled with hub 60 via flexible tubing 100 in accordance with teachings of the present disclosure. In such embodiments, connector assembly 90 may include plug 96 as described in relation to FIGS. 5A-5C. Plug 96 may be rubber, synthetic material or any material suitable for sealing connector assembly 90 and compressing to allow fluid flow when proper luer lock components are engaged.

Figures 5E, 6A, 6B:
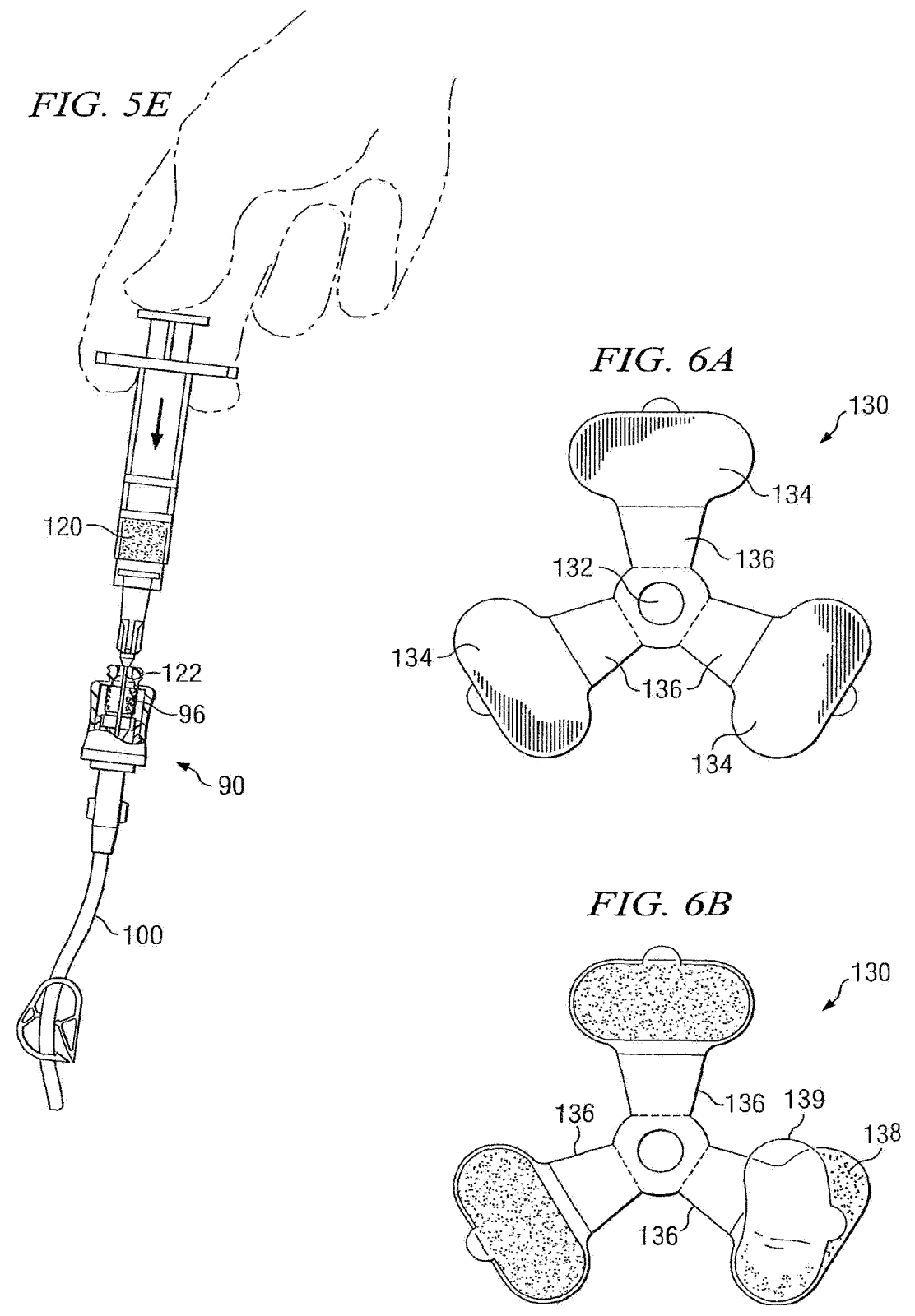

FIG. 5E shows the components of FIG. 5D during the injection of fluid from hypodermic syringe 120 into connector assembly 90. In such embodiments, hypodermic syringe 120 may include needle 122. Needle 122 may be configured to penetrate plug 96 and to allow fluid flow from hypodermic syringe 120 to hub 60 via connector assembly 90, flexible tubing 100 and right angle connector 142.

FIGS. 6A and 6B show one embodiment of supporting structure 130. For embodiments such as shown in FIGS. 6A and 6B, supporting structure 130 may include an extended surface comprising flexible wings, tabs, flaps and/or other suitable components. In such embodiments, supporting structure 130 may include any extended surface suitable for extending from central hole 132. Hole 132 may have a configuration and dimensions compatible with exterior portions of an hub 60. For example, hole 132 may be compatible with the dimensions and configuration of first end 61 of hub 60 or any other component of hub 60.

As shown in FIGS. 6A and 6B supporting structure 130 may include a plurality of wings 136 extending from hole 132. Wings 136 may be formed from any material, including but not limited to, flexible materials configured to conform to an insertion site or the exterior dimensions of an IO device or supporting structure 130. Wings 136 may include tabs 134. Tabs 134 may be formed from various types of biocompatible, flexible materials. Tabs 134 may include associated adhesive layers 138 covered by respective backing 139. Tabs 134 and associated adhesive layers 138 cooperate with each other to form an extended surface operable to releasably lock supporting structure 130 and an associated 10 device with a patient's skin proximate an insertion site.

In other embodiments supporting structure 130 may include any suitable structures for releasably engaging more than one location on a patient.

In some embodiments, such as that shown in FIGS. 6A and 6B, adhesive layers 138 may include biocompatible material for releasably attaching to a patient's skin. Backings 139 may include any structure, system or device for protecting respective adhesive layers 138 from premature exposure or premature adhesion. For example, backing 139 may include a release liner or a release material.

Supporting structure 130 such as shown in FIGS. 6A and 6B may be used with hub 60, or any other type of IO device. Supporting structure 130 may be formed from various types of elastomeric and/or nonelastomeric materials compatible with contacting skin 145 and other soft tissue covering a patient's bone at a selected insertion site or target area. The dimensions and configuration of supporting structure 130 may be selected to form satisfactory engagement with adjacent portions of a leg, an arm, or other selected target site for providing access to a patient's vascular system.

Two examples of an intraosseous device inserted into bone and associated bone marrow along with a supporting structure and attachment mechanism incorporating teachings of the present disclosure are shown in FIGS. 7A, 7B, 8A and 8B.

FIG. 7A shows an isometric view of one embodiment of an intraosseous device located in the humeral end of a patient and stabilized with a support structure, as well as connector assembly 90. In this embodiment, support structure 130 may include an extended surface, extended surface comprising three tabs 134, tabs 134 including adhesive layers 138. Adhesive layers 138 may be disposed against a patient's skin 145 in position to provide stability to intraosseous device 40. Wings 136 and tabs 134 may be formed from flexible material operable to conform with exterior portions of hub 60 and/or the configuration of an insertion site. See FIG. 7B.

As discussed in relation to FIG. 5A, connector assembly 90 may include any system or device configured to mate with hub 60 and complete a fluid network with the interior of hub 60. For instance, connector assembly 100 may include luer lock cap 140, right angle connector 142, and flexible tubing 100. In some embodiments, right angle connector 142 may comprise any hollow component configured to complete a fluid network between the interior of hub 60 and an external fluid source and/or receiver such as flexible tubing 100. For instance, right angle connector 142 may include rigid tubing, piping and/or other suitable conduits.

In some embodiments, such as that shown in FIG. 7A, luer lock cap 140 may include internal threads configured to mate with external threads 67 as well as male luer slip connector 99 configured to mate with female luer slip connector 68. Luer lock cap 140 may be further configured to assure that male luer slip connector 99 is tightly and fully engaged to provide a seal against the interior of hub 60 but allow fluid communication between the interior of hub 60 and right angle connector 142. In embodiments including flexible tubing 100, flexible tubing 100 may include any appropriate conduit for delivery of fluid, such as medical tubing and/or tubing made of polyethylene or other material.

FIG. 7B shows a cross section of the embodiment depicted in FIG. 7A, taken along line 7B-7B. As shown in FIG. 7B, an intraosseous device may be generally described as intraosseous (10) needle 70 having a hollow, longitudinal bore 73 extending therethrough. First end or tip 71 of IO needle 70 may be designed to drill or cut through bone 148 and penetrate associated bone marrow 146. Tip 71 may be open to allow communication of fluids with bone marrow 146.

Also as shown in FIG. 7B, hub 60 may include collar stop or depth limiter 150. Depth limiter 150 may be configured to limit penetration of IO needle 70 into bone marrow 146. Depth limiter 150 may include any device, feature, component and/or characteristic suitable for mating with IO needle 70 and/or hub 60. In some embodiments, such as that shown in FIG. 7B, depth limiter 150 may include a generally cylindrical component having a hollow, longitudinal bore extending therethrough. The bore of depth limiter 150 may be configured to be compatible with the external dimensions of IO needle 70.

Depth limiter 150 may include first end 152. Depth limiter 150 may be disposed along the length of IO needle 70 so that a predetermined length of IO needle 70 extends beyond first end 152. First end 152 may be configured to function as a physical stop against the exterior of bone 148 without penetrating into bone marrow 146. In such embodiments, depth limiter 150 may function to limit the penetration of needle 70 into bone marrow 146.

Depth limiter 150 may include second end 154. Second end 154 may be configured to mate with internal features of hub 60 and to fix the location of depth limiter 150 in relation to hub 60. Second end 154 may include any physical characteristic, feature, device and/or component suitable for mating with hub 60. In some embodiments, such as that shown in FIG. 7B, second end 154 may include a flared portion extending away from the generally cylindrical configuration. In alternative embodiments, hub 60 may not include depth limiter 150.

Figure 8A:
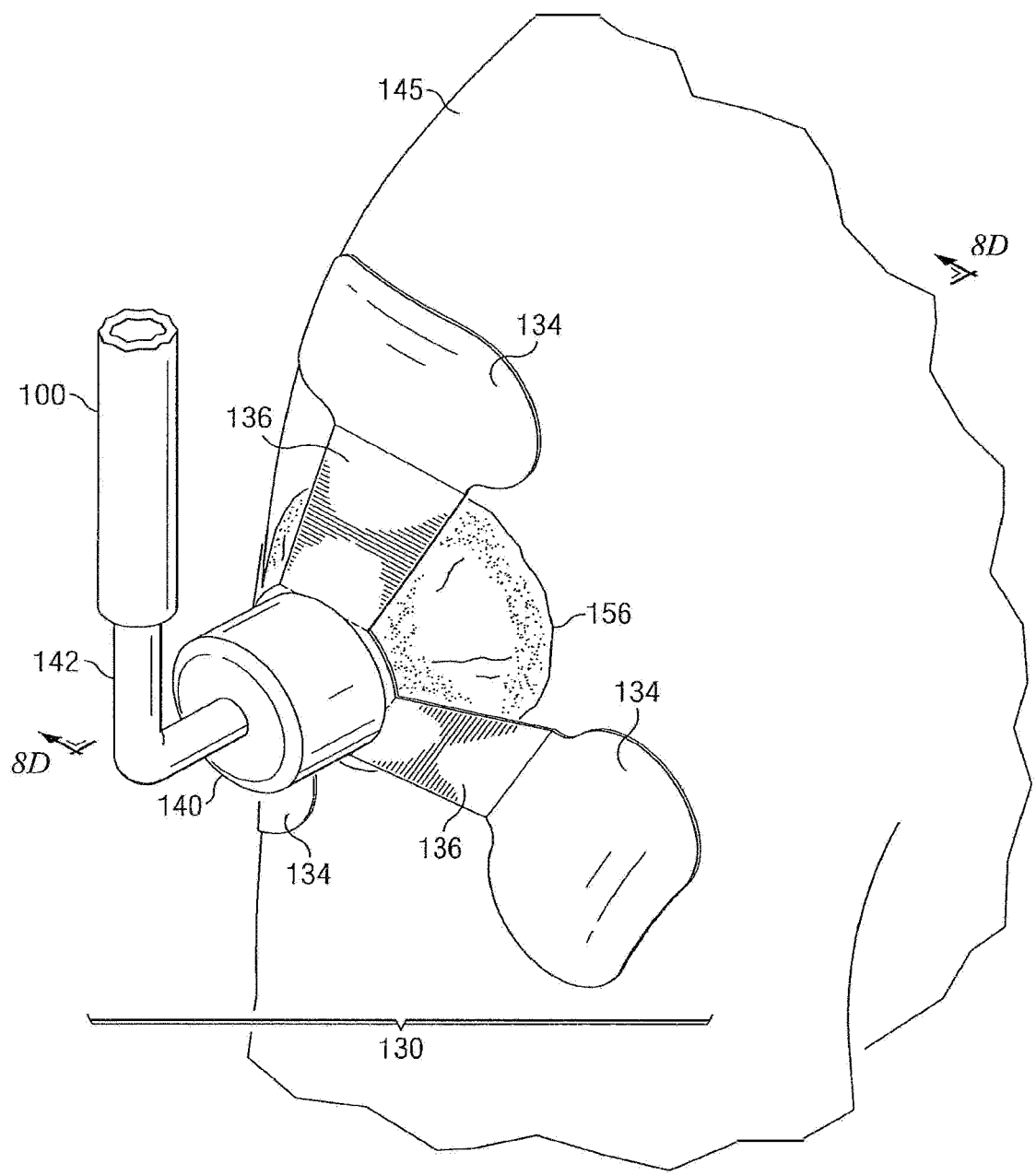
FIG. 8A is a schematic drawing showing an isometric view of another supporting structure which may be used with an intraosseous device in accordance with teachings of the present disclosure.

FIG. 8A shows an isometric view of another embodiment of support structure 130, with an intraosseous device located in the humeral head of the patient. In such embodiments, supporting structure 130 may be used to stabilize hub 60 and limit excessive movement relative to bone 148. For some applications portions of supporting structure 130 such as hollow ring or collar 156 may be placed at an insertion site prior to installing hub 60. Hub 60 may then be inserted through central hole 132 of supporting structure 130.

FIG. 8B shows a cross section of a component of an embodiment of the present disclosure. In embodiments such as that shown in FIG. 8B, supporting structure 130 may include relatively short, hollow ring 156. Hollow ring 156 may be formed from material with sufficient strength to prevent undesired movement of hub 60. Interior dimensions of hollow ring 156 may correspond generally with exterior dimensions of hub 60 to provide a relatively snug fit therebetween. Supporting structure 130 and/or hollow ring 156 may be formed from various types of semi-rigid silicone based materials and/or materials satisfactory for providing required support to an intraosseous device.

An intraosseous device such as hub 60 may be inserted through hollow ring 156. For some applications hub 60 may first be inserted into bone marrow 146. Inside diameter 158 of hollow ring 156 may be selected to be compatible with the dimensions and configuration of second end 62 such that supporting structure 130 may be inserted over or releasably engaged with hub 60 after insertion into bone marrow 146. Alternatively, hollow ring 156 may be formed from material having sufficient flexibility to accommodate expanding to fit over the exterior of hub 60. Hollow ring 156 may have an exterior shape of a cylinder or any other geometric configuration compatible with supporting structure 130. For example, in embodiments such as that shown in FIG. 8B, hollow ring 156 may have the exterior shape of the frustum of a cone.

FIG. 8C shows the cross section of one embodiment of supporting structure 130 in accordance with the present disclosure. In such embodiments, supporting structure 130 may include hollow ring 156 as shown in FIG. 8B. Supporting structure 130 may include a plurality of flaps, tabs 134 and/or wings 136 extending therefrom. Tabs 134 may be formed from relatively flexible material which will conform with adjacent portions of a patient's skin, soft tissue and bone. Tabs 134 may include adhesive layer 138 covered by backing 139.

FIG. 8D shows a cross section taken along line 8D-8D of hub 60 with associated cannula 70 inserted into bone marrow 146 through hollow ring 156 of support structure 130 as depicted in FIG. 8A. In embodiments such as shown in FIG. 8D, adhesive patches 138 may provide multiple attachment points connecting support structure 130 to the patient's skin 145. Tabs 134 and associated adhesive layers may cooperate with each other to releasably lock hollow ring 156 and an associated 10 device with skin 145. The structural stability provided by hollow ring 156 in combination with multiple attachment points may be used to stabilize hub 60 and limit excessive movement relative to bone 148.

FIGS. 9A-11C illustrate several embodiments of an apparatus for supporting an intraosseous device. Such apparatus may include inner collar 160 configured to fit over hub 60 and outer collar 162 configured to mate with inner collar 160. In such embodiments, outer collar 162 may be formed with an opening configured to mate with the exterior dimensions of inner collar 160. Outer collar 162 and inner collar 160 may further include any device or system operable to releasably connect the two components. For example, interior portions of outer collar 162 may include physical features (e.g., detents, grooves, and/or notches) configured to mate with complementary features on inner collar 160. In some embodiments, outer collar 162 may be operable to slide down against the skin at the target site to provide stability when fixed in position relative to inner collar 160.

In some embodiments, outer collar 162 may include one or more tubing clips 168. Tubing clips 168 may be any device or structure configured to restrain medical tubing and/or any other material that may be connected to intraosseous device. For example, as shown in FIG. 9A, tubing clips 168 may comprise projections from the main body of outer collar 162 curved to restrain movement of any tubing, cable or any other device engaged with tubing clips 168.

Figure 9A:
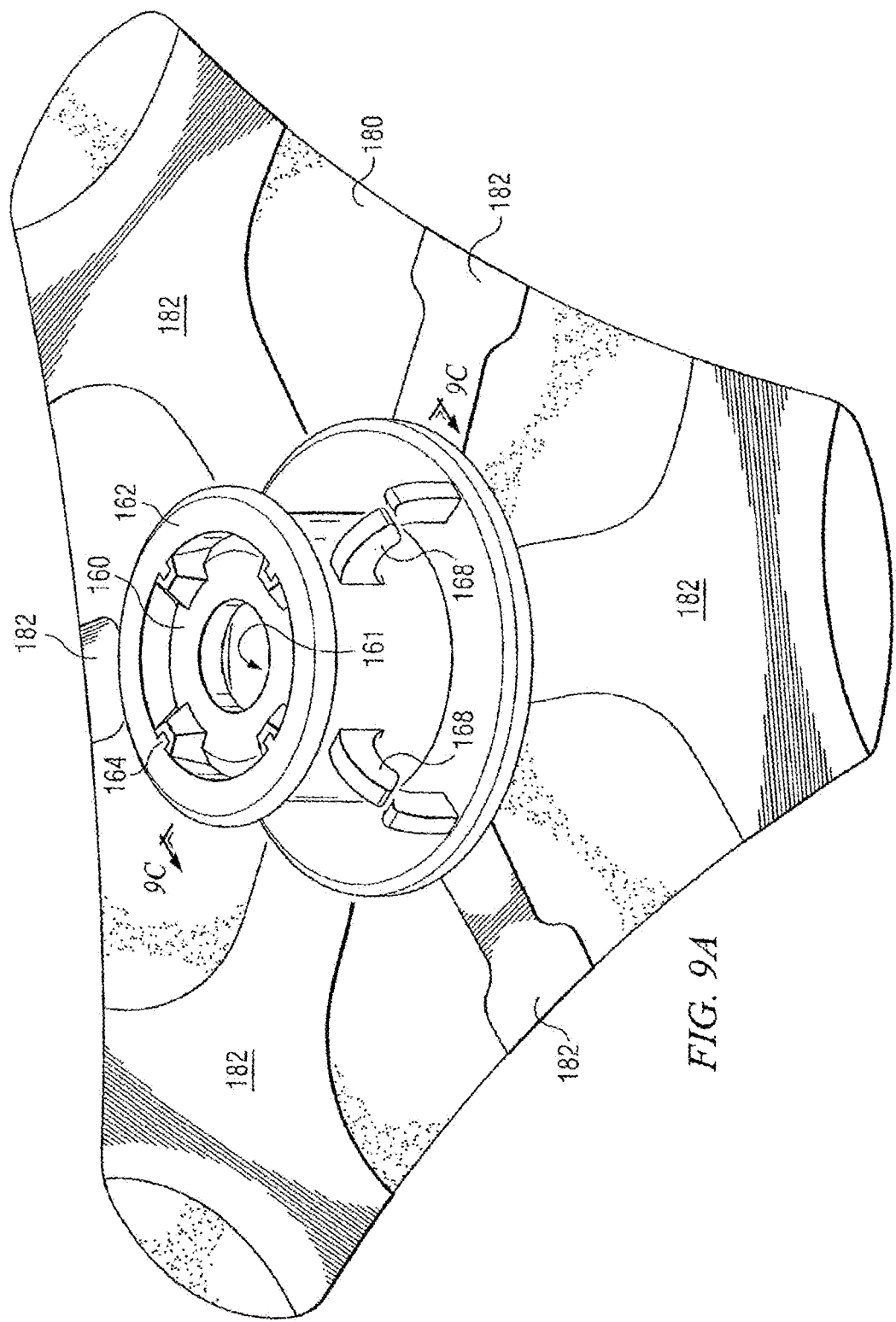
FIG. 9A is a schematic drawing showing an isometric view of another embodiment of a support structure in a first position for an intraosseous device in accordance with teaching of the present disclosure.

FIG. 9A shows an embodiment of an apparatus for supporting an intraosseous device. In such embodiments, inner collar 160 and outer collar 162 may include bore 161 extending through cylindrical shapes. Inner collar 160 and outer collar 162 may be configured so that inner collar 160 fits inside an opening in outer collar 162. In some embodiments, such as that shown in FIG. 9A, outer collar 162 may include one or more projections 164 operable to restrain the movement of inner collar 160 through the opening formed in outer collar 162.

FIG. 9A also depicts one embodiment of extended surface 180. In some embodiments, extended surface 180 may include a thin layer of flexible material configured to adapt to the contours of a patient's body. In other embodiments, extended surface 180 may be made up discrete tabs or prongs which may provide multiple attachment points. In still other embodiments, extended surface 180 may include bottom face 174 of outer collar 162. In embodiments such as that shown in FIG. 9A, extended surface 180 may include six wings 182 and may be made of elastic material connected to extended surface 180. Wings 182, in such embodiments, may serve to provide additional support to outer collar 162 and hub 60. Extended surface 180 may include adhesive layer 138 (on the reverse of 180 in FIG. 9A). Adhesive layer 138 may be protected from exposure by backing 139.

Figure 9B:
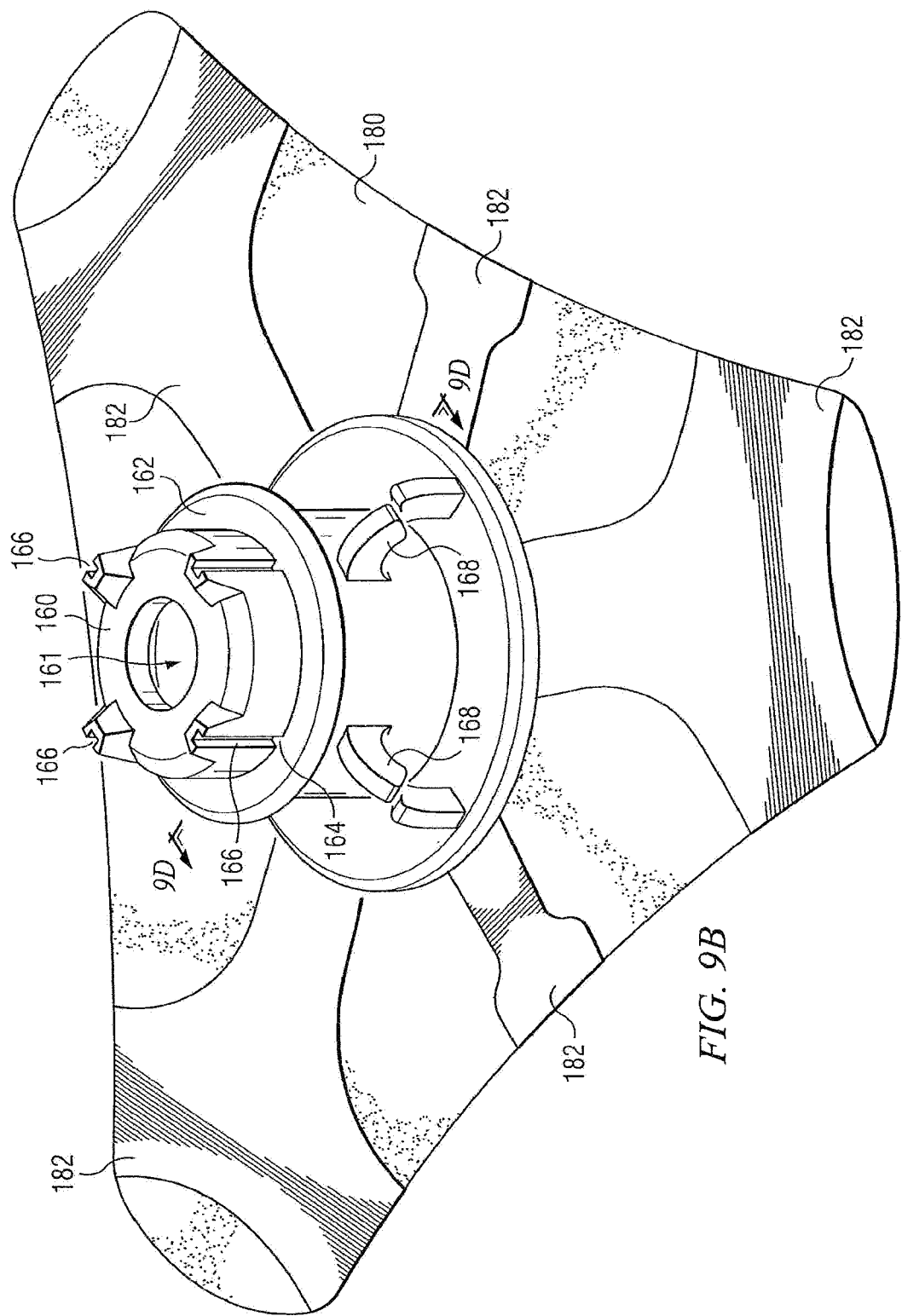
FIG. 9B is an isometric view of the support structure of FIG. 9A in a second position.

FIG. 9B shows an isometric projection of an intraosseous device support structure according to an embodiment of the disclosure and previously discussed with respect to FIG. 9A. In FIG. 9B, inner collar or core collar 160 is shown extending from outer collar 162, prior to its complete insertion as shown in FIG. 9A. In such embodiments, outer collar 162 may include tubing clips 168, discussed in greater detail with respect to FIG. 9A.

Figure 9C:
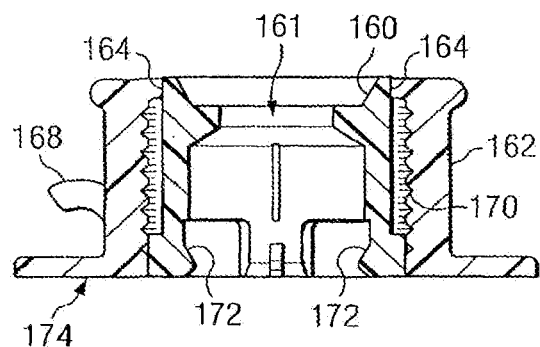
FIG. 9C is a schematic drawing in section taken along line 9C-9C of FIG. 9A.

FIG. 9C shows a cross section of an intraosseous device support structure according to an embodiment of the disclosure, taken along the line 9C-9C shown in FIG. 9B. In such embodiments, inner collar or core collar 160 may have an interior opening configured to mate with exterior dimensions of hub 60.

Figure 9D:
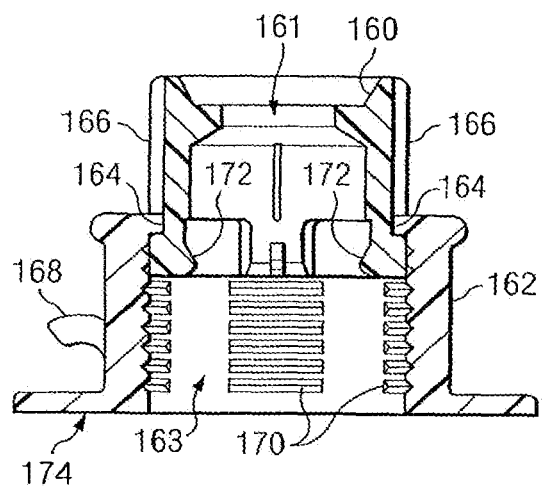
FIG. 9D is a schematic drawing in section taken along line 9D-9D of FIG. 9B.

As shown in FIGS. 9A-9D, outer collar 162 may include projections 164. Projections 164 may be configured to slide within vertical grooves 166 on the exterior of inner collar 160. In some embodiments, such as those shown in FIGS. 9A-9D, projections 164 may prevent inner collar 160 from spinning or rotating relative to outer collar 162. In addition, in embodiments where vertical grooves 166 do not extend the full length of inner collar 160, projections 164 may prevent inner collar 160 from sliding vertically upward out of outer collar 162. An example of this limit on longitudinal movement is best depicted in FIG. 9D.

Inner collar 160 may also include pawls 172. Pawls 172 may be operable to engage with locking grooves 170 formed on inside of outer collar 162. In such embodiments, locking grooves 170 and pawls 172 may be operable to fix the depth of insertion of inner collar 160 into outer collar 162.

FIGS. 9C and 9D further depict pawls 172 included in inner collar 160. Pawls 172 may be any physical or geometric feature configured to protrude from the inner diameter of inner collar 160, and further configured to flex outward when hub 60 is placed within inner collar 160. In embodiments such as those shown in FIGS. 9A-9D, pawls 172 may be configured to flex outward and engage grooves 170 on the interior of outer collar 162. In such embodiments, the interaction between pawls 172 and grooves 170 may be operable to fix the longitudinal position of inner collar 160 in relation to outer collar 162.

In embodiments including pawls 172, inner collar 160 may comprise a flexible material, such as an elastic polymer or plastic. Inner collar 160 may include notches 169 (clearly shown in FIGS. 12A-12D) configured to increase the physical deflection of pawls 172 upon application to hub 60.

FIG. 9D shows a cross section of an intraosseous device support structure according to an embodiment of the disclosure, taken through the line 9D-9D shown in FIG. 9B. In FIG. 9C, core 160 has been fully inserted into outer collar 162. In FIG. 9D, inner collar 160 has not yet been fully inserted into outer collar 162.

Figure 10A:
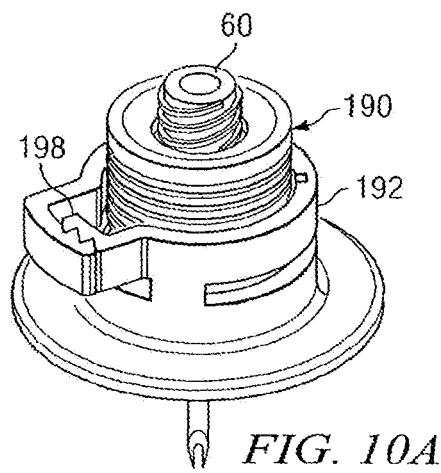
FIG. 10A is an isometric view of another embodiment of a support structure with an intraosseous device disposed therein in accordance with teaching of the present disclosure.
Figure 10B:
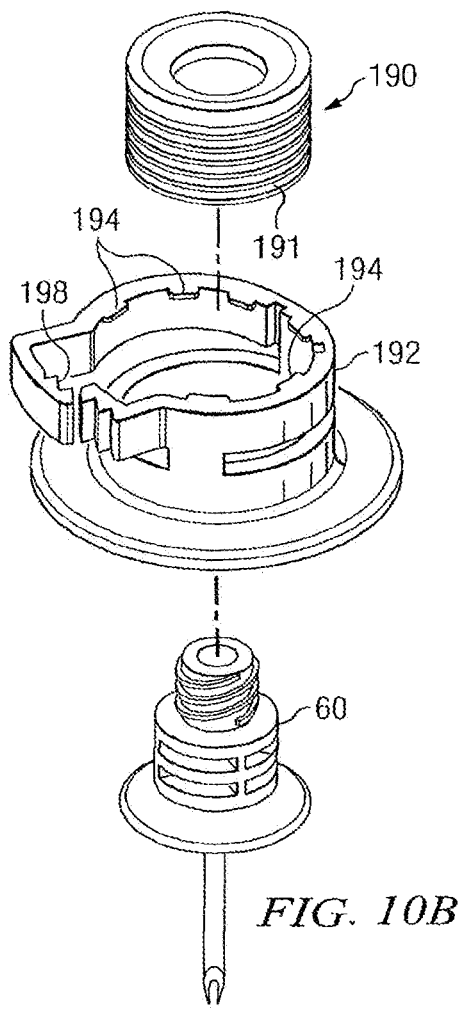
FIG. 10B is a schematic drawing showing an exploded view of the supporting structure and intraosseous device of FIG. 10A.

FIG. 10A and FIG. 10B show a close-up isometric view of an embodiment of the disclosure including hub 60, inner collar 190 and outer collar 192. In one embodiment, as shown in FIG. 10B, outer collar 192 may include teeth 194. Teeth 194 may be any physical feature configured to engage grooves 191 on inner collar 190. Outer collar 192 may be configured to have an adjustable inner diameter. The inner diameter of outer collar 192 may be configured to reduce in response to force applied to the outer diameter of outer collar 192, as in the embodiment depicted in FIG. 10B. Reduction of the internal diameter of outer collar 192 may result in teeth 194 protruding between grooves 191 and holding inner collar 190 in place against longitudinal and/or rotational displacement.

Outer collar 192 may include additional physical features configured to maintain a reduced inner diameter even after the external force is removed. For example, outer collar 192 may include snap-grip 198. Snap-grip 198 may be operable to reduce the diameter of outer collar 192 as snap-grip 198 is squeezed closed. Snap-grip 198 may include any feature operable to restrain the outer collar 192 from increasing the distance between teeth 194 once reduced. Snap-grip 198 may be operable to release outer collar 192 as snap-grip 198 is twisted open.

Figure 11A:
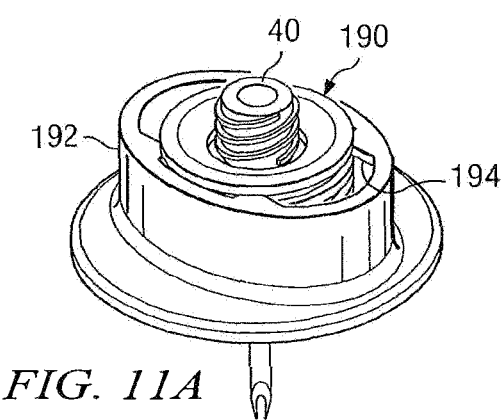
FIG. 11A is a schematic drawing showing an isometric view of another support structure with an intraosseous device disposed therein in accordance with teaching of the present disclosure.
Figure 11C:
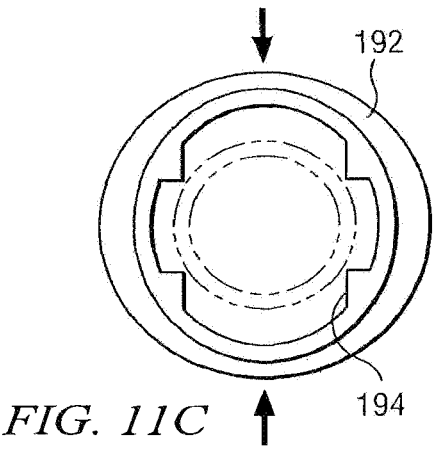
FIG. 11C is a schematic drawing showing a plane view of the supporting structure of FIG. 11A.
Figure 11B:
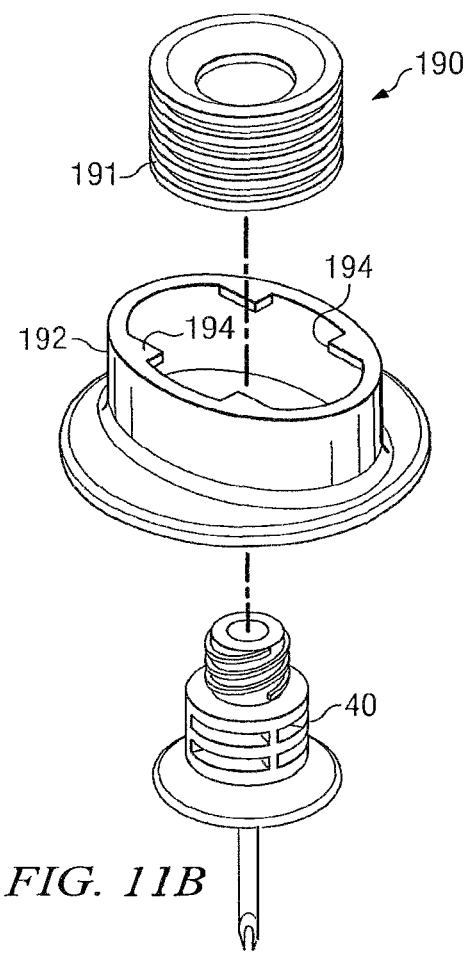
FIG. 11B is a schematic drawing showing an exploded view of supporting structure and intraosseous device of FIG. 11A.

FIGS. 11A-11C show a close-up isometric view of another embodiment of the disclosure which includes a device to adjust the inner diameter of outer collar 192. In such embodiments, outer collar 192 may be formed as an ellipse and may be formed out of flexible material. Outer collar 192 may include teeth 194 configured to engage grooves 191 on inner collar 190 in the absence of an external force. Outer collar 192 may include teeth 194 on only the long sides of the ellipse. In such embodiments, force applied to the long axis (as shown by the arrows in FIG. 11C) of the outer collar 192 may operate to increase the distance between teeth 194 and release inner collar 190.

FIGS. 12A-12D depict a cross section of another embodiment of the present disclosure. FIGS. 12A-12D demonstrate the sequential implementation of one such embodiment, including hub 60, luer lock cap 140 and other components. In such embodiments, IO support structure 130 may additionally comprise any of the elements disclosed or discussed in the earlier sections of the current disclosure.

FIGS. 12A-12D shows one embodiment of IO support structure 130 including hub 60, luer lock cap 140 and right angle connector 142, all of which are discussed in greater detail in relation to FIGS. 7 and 8. In embodiments such as that shown in FIG. 12, IO support device 130 may further incorporate inner collar 160 and outer collar 162, discussed in greater detail in relation to FIGS. 9, 10 and 11.

Figure 12A:
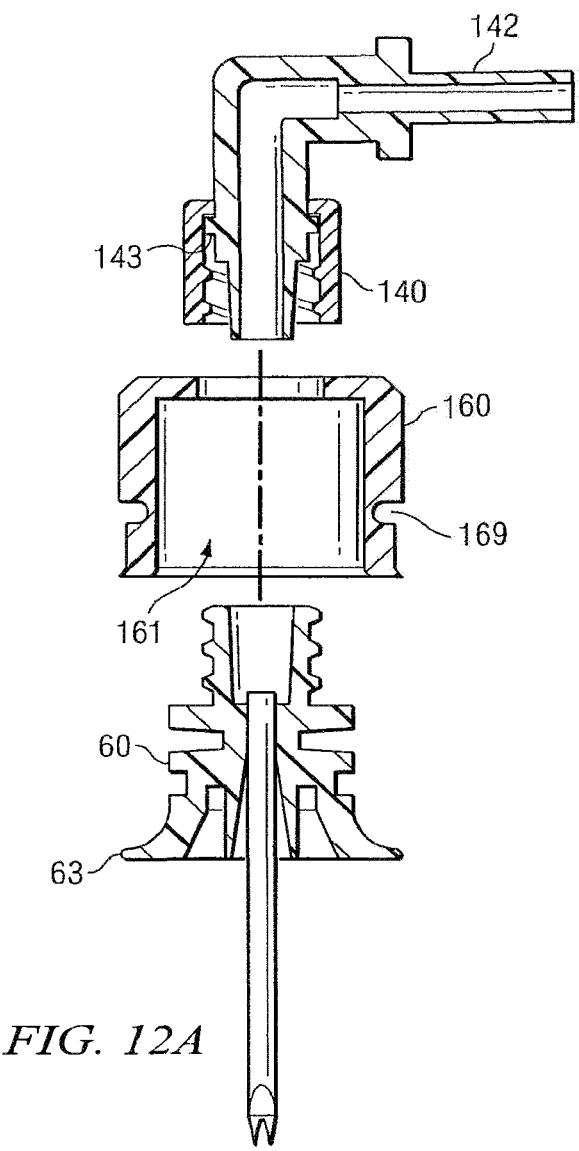
FIG. 12A is a schematic drawing in section showing portions of another embodiment of a support structure for an intraosseous device in accordance with teaching of the present disclosure, showing an exploded view of the support structure.

FIG. 12A shows an exploded view of one embodiment of IO support device 130, in preparation for assembly. FIG. 12B shows the same components after inner collar 160 has been placed around hub 60 and positioned so that first end 61 protrudes beyond inner collar 160. Pawls 172 are also shown in this first, retracted position. FIG. 12C shows the assembly of FIG. 12B after luer lock cap 140 has been attached to first end 61 of hub 60. Pawls 172 are shown in their second, radially expanded position. In some embodiments, such as that shown in FIGS. 12A-12D, hub 60 may include external threads 67 configured to mate with internal threads on luer lock cap 140. When a user screws luer lock cap 140 to external threads 67 of hub 60, the compressive force applied to hub 60 secures the male luer slip connections 99 on the luer lock cap 140 into the female luer slip connections 68 of first end 61 preventing leakage of fluid as more fully discussed in FIGS. 5A-5E.

At the same time, the attachment of luer lock cap 140 to hub 60 pushes inner collar 160 in place in relation to hub 60. Luer lock cap 140 may be configured so as to rotate freely around right angle connector 142. Luer lock cap 140 may be restricted against longitudinal movement by steps 143 included in right angle connector 142. In addition, in embodiments such as those depicted in FIGS. 12A-12D, threading of luer lock cap 140 onto hub 60 forces inner collar 160 downward onto hub 60. As depicted in FIGS. 12B and 12C, inner collar 160 may include inner diameter 161 configured to mate with exterior features of hub 60.

In such embodiments, the attachment of luer lock cap 140 may push inner collar 160 downward onto flange 63 on hub 60. Inner collar 160 may include, as discussed in relation to FIGS. 9A-9D, pawls 172 configured to flex outward in relation to inner collar 160. In such embodiments, flange 63 forces pawls 172 to flex outward from inner collar 160.

FIG. 12D shows the assembly of FIG. 12C placed in relation to outer collar 162. In such embodiments, inner collar 160 and outer collar 162 may include any combination of components, including but not limited to those discussed in relation to FIGS. 9-11. In embodiments such as that shown in FIG. 12D, inner collar 160 may include pawls 172. Joining luer lock cap 140 to hub 60 may including forcing inner collar 160 onto flange 63, thereby extending pawls 172 outward from inner collar 160. As shown in FIG. 12D, pawls 172 may be configured to extend into grooves 170 on outer collar 162, thereby fixing the longitudinal position of inner collar 160 in relation to outer collar 162.

In alternative embodiments, outer collar 162 may not include grooves 170. In such embodiments, pawls 172 may be configured to extend outward and operate as a friction lock with inner diameter 163 of outer collar 162. In such embodiments, inner diameter 163 may include any feature (e.g., a rough surface) such that inner diameter 163 and pawls 172 may be operable to form an effective lock against longitudinal movement between inner collar 160 and outer collar 162.

A person having ordinary skill in the art will recognize that the longitudinal position of inner collar 160 in relations to outer collar 162 may be purposefully varied to accommodate various applications. For example, if the target insertion site for the IO device includes bone with a small and/or soft cortex, the bone itself may not provide much lateral support for hub 60 once inserted. Second end 62 of hub 60 may contact skin 145 in isolated points or not at all. In such cases, outer collar 162 may intentionally extend downward well beyond inner collar 160 in order to provide significant extra stabilization, especially when used at insertion sites where the skin soft tissue layer is relatively thin. Outer collar 162 may include bottom face 174. Bottom face 174 may include any treatment intended to improve contact between outer collar 162 and target insertion site. For example, bottom face 174 may include any biocompatible adhesive material configured to adhere bottom face 174 to skin 145. In embodiments including depth limiter 150, depth limiter 150 may restrict the insertion depth of cannula 70 to the extent that hub 60 does not contact skin 145. In such embodiments, outer collar 162 may provide extra stabilization when extending downward beyond hub 60 and/or inner collar 160.

Although the present disclosure and its advantages have been described in relation to intraosseous devices, it should be clear to a person having ordinary skill in the art that these teachings can be applied to support a variety of medical devices in relation to a patient. For example, embodiments of the present disclosure might be utilized to support any intravenous connection or device, a central line, an endotracheal tube, a chest tube, a catheter, dialysis tubing and/or any other device intended to make a fluid connection to one or more systems of the patient.

Examples of acute and chronic conditions which may be treated using intraosseous devices and procedures incorporating teachings of the present disclosure include, but are not limited to, the following:

Anaphylaxis (epinephrine, steroids, antihistamines, fluids, and life support);
Arrhythmia (anti-arrhythmics, electrolyte balance, life support);
Burns (fluid replacement, antibiotics, morphine for pain control);
Cardiac arrest (epinephrine, atropine, amiodarone, calcium, xylocalne, magnesium);
Congestive heart failure (life support, diuretics, morphine, nitroglycerin);
Dehydration (emergency port for life support, antibiotics, blood, electrolytes);
Diabetic Ketoacidosis (life support, electrolyte control, fluid replacement);
Dialysis (emergency port for life support, antibiotics, blood, electrolytes);
Drug overdose (naloxone, life support, electrolyte correction);
Emphysema (life support, beta adrenergics, steroids);
Hemophiliacs (life support, blood, fibrin products, analgesics);
Osteomyelitis (antibiotics directly into the site of infection, analgesics);
Pediatric applications (shock, dehydration, nutrition, electrolyte correction);
Seizures (anti-seizure medications, life support, fluid balance);
Shock (life support fluids, pressor agents, antibiotics, steroids);
Sickle cell crisis (fluid, morphine for pain, blood, antibiotics);
Trauma (emergency port for life support fluids, antibiotics, blood, electrolytes);

Although the present disclosure and its advantages have been described in detail, it should be understood that various changes, substitutions and alternations can be made herein without departing from the spirit and scope of the disclosure as defined by the following claims.

What is claimed is:

1. An apparatus for supporting an intraosseous device disposed at a target site in a patient, the apparatus comprising:
    an inner support including a bore extending therethrough, the bore configured to receive a portion of the intraosseous device; and
    an outer support including an adjustable inner diameter, the outer support configured to receive a portion of the inner support;
    wherein an outer surface of the inner support includes a first engagement portion including at least one groove, an inner surface of the outer support includes a second engagement portion including at least one tooth, and the first and second engagement portions are configured to engage each other to secure the inner support in place against longitudinal and rotational displacement relative to the outer support;
    wherein a reduction of the inner diameter of the outer support secures the inner support in place against the longitudinal and/or rotational displacement; and
    wherein the reduction of the inner diameter of the outer support results in the at least one tooth protruding into the at least one groove to hold the inner support in place against the longitudinal and/or rotational displacement.

2. The apparatus according to claim 1, wherein the outer support includes a snap-grip operable to reduce the diameter of the outer support as the snap-grip is squeezed closed.

3. The apparatus according to claim 2, wherein the snap-grip is configured to restrain the outer support from increasing a distance between opposing teeth of the at least one tooth once reduced.

4. The apparatus according to claim 3, wherein the snap-grip is configured to release the outer support as the snap-grip is twisted open.

5. The apparatus according to claim 1, wherein the inner diameter of the outer support is configured to reduce in response to a force applied to the outer diameter of the outer support.

6. The apparatus according to claim 1, wherein the outer support is formed from flexible material.

7. The apparatus according to claim 6, wherein the outer support is movable between a first position configured to receive the inner support and a second position configured to secure the inner support.

8. The apparatus according to claim 7, wherein the outer support defines a bore having a circular-shaped cross section when the outer support is in the second position.

9. The apparatus according to claim 7, wherein the outer support defines a bore having an elliptical-shaped cross section when the outer support is in the second position.

10. The apparatus according to claim 9, wherein the at least one tooth of the outer support is located on a long side of the elliptical-shaped bore.

11. The apparatus according to claim 9, wherein a force applied to a long axis of the outer support increases a distance between opposing teeth of the at least one tooth to release the inner support.

12. An apparatus for supporting an intraosseous device disposed at a target site in a patient, the apparatus comprising:
    an inner support including a bore extending therethrough, the bore configured to receive a portion of the intraosseous device; and
    an outer support including an adjustable inner diameter, the outer support configured to receive a portion of the inner support;
    wherein an outer surface of the inner support includes a first engagement portion, an inner surface of the outer support includes a second engagement portion, and the first and second engagement portions are configured to engage each other to secure the inner support in place against longitudinal and rotational displacement relative to the outer support;
    wherein a reduction of the inner diameter of the outer support secures the inner support in place against the longitudinal and/or rotational displacement;
    wherein the outer support is formed from flexible material;
    wherein the outer support is movable between a first position configured to receive the inner support and a second position configured to secure the inner support; and
    wherein the outer support defines a bore having an elliptical-shaped cross section when the outer support is in the second position.

13. The apparatus according to claim 12, wherein the outer support includes at least one tooth configured to engage at least one groove on the inner support in the absence of an external force.

14. The apparatus according to claim 13, wherein the at least one tooth of the outer support is located on a long side of the elliptical-shaped bore.

15. The apparatus according to claim 13, wherein a force applied to a long axis of the outer support increases a distance between opposing teeth of the at least one tooth to release the inner support.

* * * * *